United States Patent
Hlavinka et al.

(10) Patent No.: US 9,725,393 B2
(45) Date of Patent: *Aug. 8, 2017

(54) METHODS FOR THE PRODUCTION OF α,β-UNSATURATED CARBOXYLIC ACIDS AND SALTS THEREOF

(71) Applicant: Chevron Phillips Chemical Company LP, The Woodlands, TX (US)

(72) Inventors: Mark L. Hlavinka, Tulsa, OK (US); Max P. McDaniel, Bartlesville, OK (US); Pasquale Iacono, Bartlesville, OK (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/091,794

(22) Filed: Apr. 6, 2016

(65) Prior Publication Data

US 2016/0229782 A1    Aug. 11, 2016

Related U.S. Application Data

(63) Continuation-in-part of application No. 14/509,082, filed on Oct. 8, 2014.

(51) Int. Cl.
| | |
|---|---|
| *C07C 51/15* | (2006.01) |
| *C07C 51/377* | (2006.01) |
| *B01J 31/12* | (2006.01) |
| *B01J 31/14* | (2006.01) |
| *B01J 31/22* | (2006.01) |
| *B01J 31/26* | (2006.01) |
| *B01J 31/38* | (2006.01) |
| *C07C 51/09* | (2006.01) |

(52) U.S. Cl.
CPC ............. *C07C 51/15* (2013.01); *B01J 31/128* (2013.01); *B01J 31/143* (2013.01); *B01J 31/2234* (2013.01); *B01J 31/2295* (2013.01); *B01J 31/26* (2013.01); *B01J 31/38* (2013.01); *C07C 51/09* (2013.01); *C07C 51/377* (2013.01); *B01J 2231/321* (2013.01); *B01J 2231/46* (2013.01); *B01J 2531/847* (2013.01)

(58) Field of Classification Search
CPC ....... C07C 51/15; C07C 51/377; C07C 57/04; B01J 2231/46; B01J 2531/847; B01J 31/128; B01J 31/143; B01J 31/2295; B01J 31/26; B01J 31/38
USPC .................................. 562/551, 599
See application file for complete search history.

(56) References Cited

U.S. PATENT DOCUMENTS

| | | |
|---|---|---|
| 4,060,480 A | 11/1977 | Reed |
| 4,452,910 A | 6/1984 | Hopkins |
| 5,376,611 A | 12/1994 | Shveima |
| 6,107,230 A | 8/2000 | McDaniel et al. |
| 6,165,929 A | 12/2000 | McDaniel et al. |
| 6,294,494 B1 | 9/2001 | McDaniel et al. |
| 6,300,271 B1 | 10/2001 | McDaniel et al. |
| 6,316,553 B1 | 11/2001 | McDaniel et al. |
| 6,355,594 B1 | 3/2002 | McDaniel et al. |
| 6,376,415 B1 | 4/2002 | McDaniel et al. |
| 6,388,017 B1 | 5/2002 | McDaniel et al. |
| 6,391,816 B1 | 5/2002 | McDaniel et al. |
| 6,395,666 B1 | 5/2002 | McDaniel et al. |
| 6,524,987 B1 | 2/2003 | Collins et al. |
| 6,548,441 B1 | 4/2003 | McDaniel et al. |
| 6,548,442 B1 | 4/2003 | McDaniel et al. |
| 6,576,583 B1 | 6/2003 | McDaniel et al. |
| 6,613,712 B1 | 9/2003 | McDaniel et al. |
| 6,632,894 B1 | 10/2003 | McDaniel et al. |
| 6,667,274 B1 | 12/2003 | Hawley et al. |
| 6,750,302 B1 | 6/2004 | McDaniel et al. |
| 7,250,510 B2 | 7/2007 | Organ et al. |
| 7,294,599 B2 | 11/2007 | Jensen et al. |
| 7,601,665 B2 | 10/2009 | McDaniel et al. |
| 7,884,163 B2 | 2/2011 | McDaniel et al. |
| 8,309,485 B2 | 11/2012 | Yang et al. |
| 8,592,632 B2 | 11/2013 | Dahmen et al. |
| 8,623,973 B1 | 1/2014 | McDaniel et al. |
| 8,642,803 B2 | 2/2014 | Limbach et al. |
| 8,697,909 B2 | 4/2014 | Limbach et al. |
| 8,703,886 B1 | 4/2014 | Yang et al. |

(Continued)

FOREIGN PATENT DOCUMENTS

| | | |
|---|---|---|
| CN | 103785469 | 5/2014 |
| CN | 104418719 | 3/2015 |

(Continued)

OTHER PUBLICATIONS

Hendricksen "Catalytic Formation of Acrylate from Carbon Dioxide and Ethene" Chemistry, A European Journal, 2014, 20, p. 12037-12040.*
Eigenberger ("Catalytic Fixed-Bed Reactors" Ullmann's Encyclopedia of Industrial Chemistry, Jul. 15, 2012, DOI: 10.1002/14356007.b04_199.pub2, p. 1-66).*
Deutschmann ("Heterogeneous Catalysis and Solid Catalysts, 2. Development and Types of Solid Catalysts" Ullmann's Encyclopedia of Industrial Chemistry, Oct. 15, 2011, DOI: 10.1002/14356007.o05_o02, p. 483-549).*
Bruckmeier et al., "Formation of Methyl Acrulate from $CO_2$ and Ethylene via Methylation of Nickelalactones," Organometallics, 2010, vol. 29, No. 10, pp. 2199-2202.

(Continued)

*Primary Examiner* — Jafar Parsa
*Assistant Examiner* — Amy C Bonaparte
(74) *Attorney, Agent, or Firm* — Merchant & Gould P.C.

(57) ABSTRACT

Processes for producing an α,β-unsaturated carboxylic acid, such as acrylic acid, or a salt thereof, using treated solid oxides are disclosed. The treated solid oxides can be calcined solid oxides, metal-treated solid oxides, or metal-treated chemically-modified solid oxides, illustrative examples of which can include sodium-treated alumina, calcium-treated alumina, zinc-treated alumina, sodium-treated sulfated alumina, sodium-treated fluorided silica-coated alumina, and similar materials.

20 Claims, No Drawings

(56) References Cited

U.S. PATENT DOCUMENTS

| | | | |
|---|---|---|---|
| 8,940,940 B2 | 1/2015 | Dehn et al. | |
| 9,023,959 B2 | 5/2015 | McDaniel et al. | |
| 9,416,087 B2 | 8/2016 | Hlavinka et al. | |
| 2010/0076167 A1* | 3/2010 | McDaniel | C08F 10/02 |
| | | | 526/130 |
| 2011/0218359 A1 | 9/2011 | Limbach | |
| 2013/0172616 A1 | 7/2013 | Limbach et al. | |
| 2015/0343431 A1 | 12/2015 | Parvulescu et al. | |
| 2015/0344394 A1 | 12/2015 | Parvulescu et al. | |
| 2016/0102039 A1 | 4/2016 | Hlavinka et al. | |
| 2016/0130208 A1 | 5/2016 | Schäffner et al. | |
| 2016/0311745 A1 | 10/2016 | Hlavinka et al. | |
| 2017/0166506 A1 | 6/2017 | Iacono et al. | |

FOREIGN PATENT DOCUMENTS

| | | |
|---|---|---|
| CN | 104418736 | 3/2015 |
| CN | 104418737 | 3/2015 |
| CN | 105622383 | 6/2016 |
| CN | 105622400 | 6/2016 |
| DE | 11 2014 001 125 A5 | 11/2015 |
| EP | 2 797 869 A4 | 8/2015 |
| IN | 201207472 P4 | 12/2013 |
| IN | 201404656 P4 | 9/2015 |
| WO | WO 2011/107559 | 9/2011 |
| WO | WO 2013/098772 | 7/2013 |
| WO | WO 2013/186238 | 12/2013 |
| WO | WO 2014/003195 | 1/2014 |
| WO | WO 2014/130410 | 8/2014 |
| WO | WO 2014/198469 | 12/2014 |
| WO | WO 2015/018793 | 2/2015 |
| WO | WO 2015/132031 | 9/2015 |
| WO | WO 2015/173276 | 11/2015 |
| WO | WO 2015/173277 | 11/2015 |
| WO | WO 2015/173295 | 11/2015 |
| WO | WO 2015/173296 | 11/2015 |
| WO | WO 2015/173307 | 11/2015 |
| WO | WO 2015/197699 | 12/2015 |

OTHER PUBLICATIONS

Fischer et al., "A key step in the formation of acrylic acid from $CO_2$ and ethylene: the transformation of a nickelalactone into a nickel-acrylate complex," Chem Commun., 2006, pp. 2510-2512.

Fischer et al., "Zur Synthese und Charakterisierung von N,N'—Tetramethylethylendiamin-nickelacyclopropionat," Z. anorg. allg. Chem., 1989, vol. 577, pp. 111-114.

Gordillo et al., "Catalytic route to acrylates from alkenes and $CO_2$," ACS Abstracts, 245th ACS National Mtg, 2013, INOR-1109, pp. 4-7 to 11.

Hoberg et al., "Nickel(O)-Induzierte C-C-Verknüpfung Zwischen Kohlendioxid und Ethylen Sowie Mono-Oder Di-Substituierten Alkenen," Journal of Organometallic Chemistry, 1983, vol. 251, pp. C51-053.

Huguet et al., "Nickel-Catalyzed Direct Carboxylation of Olefins with $CO_2$: One-Pot Synthesis of α,β-Unsaturated Carboxylic Acid Salts," Chem. Eur. J. 2014, vol. 20, pp. 16858-16862.

International Search Report and Written Opinion of the International Searching Authority, PCT/US2015/054128, dated Dec. 21, 2015, 11 pages.

Jin et al., "Effect of Sodium Cation on Metallacycle β- Hydride Elimination in $CO_2$-Ethylene Coupling to Acrylates," Chem. Eur. J., 2014, vol. 20, No. 11, pp. 3205-3211.

Jin et. al., "Lewis Acid Inducedβ- Elimination from a Nickelatactone: Efforts toward Acrylate Production from $CO_2$ and Ethylene," Department of Chemistry, Brown University, Providence RI; Department of Chemistry, Yale University, New Haven, CT; pubs.acs.org/Organometallics; 2013, pp. A-H, 8 pages.

Kirillov, "Carboxylic acid derivative via catalytic carboxylation of unsaturated hydrocarbons: whether the nature of a reductant may determine the mechanism of $CO_2$ incorporation," Dalton Transactions (2015) vol. 44, pp. 16212-16223.

Langer et al., "A new set of nickelacyclic carboxylates ("nickelalactones") containing pyridine as supporting ligand: synthesis, structures and application in C-C- and C-S linkage reactions," Journal of Organometallic Chemistry, 2004, 689, pp. 2952-2962.

Lejkowski et al., "The First Catalytic Synthesis of an Acrylate from $CO_2$ and an Alkene—A Rational Approach," Chem. Eur. J., 2012, vol. 18, pp. 14017-14025.

Limbach, et al., "CO2 as C1 building block for the synthesis of acrylates and beyond," ACS Abstracts, 247th ACS National Mtg, CATL-116, 2014, pp. 3-16 to 20.

Limbach, et al., "Investigation of fundamental steps in the formation of acrylates from CO2 and ethylene," ACS Abstracts, 243rd ACS National Mtg, 2012, INOR-1216, pp. 3-29.

Papai et al., "Mechanistic Details of Nickel(0)-Assisted Oxidative Coupling of $CO_2$ with $C_2H_4$," Chemical Research Centre of the Hungarian Academy of Sciences; Organometallics, 2004, vol. 23, pp. 5252-5259.

Pinnavaia, T. J., "Intercalated Clay Catalysts," Science, 1983, vol. 220, No. 4595, pp. 365-371.

Plessow, et al., "Acrylate Formation from CO2 and Ethylene Mediated by Nickel Complexes: A Theoretical Study," Organometallics, 2014, vol. 33, pp. 3657-3668.

Plessow, et al., "Mechanistic Details of the Nickel-Mediated Formation of Acrylates from CO2, Ethylene and Methyl Iodide," Organometallics, 2013, vol. 32, pp. 3327-3338.

Stieber, et al., "Acrylate formation from CO2 and ethylene: catalysis with palladium and mechanistic insight," Chem. Commun., 2015, vol. 51, pp. 10907-10909.

Thomas, J. M., "Sheet Silicate Intercalates: New Agents for Unusual Chemical Conversions*," Intercalation Chemistry, Academic Press, Inc., 1982, Ch. 3, pp. 55-99.

Yu, "Carboxylation of olefins/alkynes with $CO_2$ to industrially relevant acrylic acid derivatives," Journal of $CO_2$ Utilization (2013) pp. 60-68.

U.S. Appl. No. 15/203,844, filed Jul. 7, 2016 entitled "Methods for the Production of α,β-Unsaturated Carboxylic Acids and Salts Thereof".

Knopf et al., entitled "*A family of cis-macrocyclic diphosphines: modular, stereoselective synthesis and application in catalytic $CO_2$/ ethylene coupling*," RSC, Chemical Science, 2016, 6 pages.

Manzini et al., entitled "*Enhanced activity and recyclability of palladium complexes in the catalytic synthesis of sodium acrylate from $CO_2$ and ethylene*," ChemCatChem 10.1002/cctc.201601150, Wiley-vch, 2016, 9 pages.

Manzini et al., entitled "*Palladium- and Nickel-Catalyzed Synthesis of Sodium Acrylate from Ethylene, $CO_2$ and Phenolate Bases: Optimization of the Catalytic System for a Potential Process*," Eur J. Org. Chem., 2015, pp. 7122-7130.

Manzini et al., entitled "*Synthesis of acrylates from olefins and $CO_2$ using sodium alkoxides as basis*," Catal. Today, Elsevier B.V., 2016, 8 pages.

Al-Ghamdi et al., entitled "*Structure Activity relationship to Screen Ni-Bisphosphine Complexes for the Oxidative Coupling of $CO_2$ and Ethylene*," Organometallics, 2017, vol. 36, pp. 1107-1112.

* cited by examiner

METHODS FOR THE PRODUCTION OF α,β-UNSATURATED CARBOXYLIC ACIDS AND SALTS THEREOF

REFERENCE TO RELATED APPLICATION

This application is a continuation-in-part application of U.S. patent application Ser. No. 14/509,082, filed on Oct. 8, 2014, now U.S. Pat. No. 9,416,087, the disclosure of which is incorporated herein by reference in its entirety.

BACKGROUND OF THE INVENTION

The majority of industrially synthesized chemical compounds are prepared from a limited set of precursors, whose sources are ultimately fossil fuels. It would be beneficial to use a renewable resource, such as carbon dioxide, which is a non-toxic, abundant, and economical $C_1$ synthetic unit. The coupling of carbon dioxide and olefins holds tremendous promise as one could envision the direct preparation of acrylates and carboxylic acids through this method. Currently, acrylic acid is produced via a two-stage oxidation of propylene. The production of acrylic acid directly from carbon dioxide and ethylene would represent a significant improvement due to the greater availability of ethylene and carbon dioxide versus propylene, the use of a renewable material ($CO_2$) in the synthesis, and the replacement of the two-step oxygenation process currently being practiced. Accordingly, it is to these ends that the present invention is directed.

SUMMARY OF THE INVENTION

Processes for producing an α,β-unsaturated carboxylic acid, or a salt thereof, are disclosed herein. These processes represent an improvement over homogeneous processes that result in poor yields and have challenging separation/isolation procedures, due in part to the reaction being conducted in an organic solvent, making isolation of the desired α,β-unsaturated carboxylic acid (e.g., acrylic acid) difficult. In contrast, the processes disclosed herein utilize a solid promoter (or solid activator, such as a treated solid oxide), providing a heterogeneous system that has a distinct advantage in ease of separation of the desired product from the catalytic promoter. Moreover, the solid promoters can result in surprisingly high yields of the desired acrylate or α,β-unsaturated carboxylic acid, such as acrylic acid.

In accordance with aspects of the present invention, one such process for producing an α,β-unsaturated carboxylic acid, or a salt thereof, can comprise:
(1) contacting
   (a) a metallalactone;
   (b) a diluent; and
   (c) a solid promoter (e.g., a treated solid oxide);
(2) forming an adduct of an α,β-unsaturated carboxylic acid adsorbed onto the solid promoter; and
(3) treating the adduct adsorbed onto the solid promoter to produce the α,β-unsaturated carboxylic acid, or the salt thereof.

In another aspect of this invention, a process for producing an α,β-unsaturated carboxylic acid, or a salt thereof, is provided, and in this aspect, the process can comprise:
(I) contacting
   (i) a transition metal-ligand complex;
   (ii) an olefin;
   (iii) carbon dioxide ($CO_2$);
   (iv) a diluent; and
   (v) a solid promoter (e.g., a treated solid oxide); and
(II) forming the α,β-unsaturated carboxylic acid, or the salt thereof.

Yet, in another aspect of this invention, a process for performing a metallalactone elimination reaction is provided, and in this aspect, the process can comprise:
(1) contacting
   (a) a metallalactone;
   (b) a diluent; and
   (c) a solid promoter (e.g., a treated solid oxide); and
(2) forming an α,β-unsaturated carboxylic acid, or a salt thereof.

In these and other aspects, the processes disclosed herein can be used to produce, for instance, acrylic acid or a salt thereof.

Both the foregoing summary and the following detailed description provide examples and are explanatory only. Accordingly, the foregoing summary and the following detailed description should not be considered to be restrictive. Further, features or variations may be provided in addition to those set forth herein. For example, certain aspects may be directed to various feature combinations and sub-combinations described in the detailed description.

DEFINITIONS

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, $2^{nd}$ Ed (1997) can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

While compositions and methods are described in terms of "comprising" various components or steps, the compositions and methods can also "consist essentially of" or "consist of" the various components or steps, unless stated otherwise. For example, a step in certain processes consistent with the present invention can contact components comprising a metallalactone, a diluent, and a treated solid oxide; alternatively, can contact components consisting essentially of a metallalactone, a diluent, and a treated solid oxide; or alternatively, can contact components consisting of a metallalactone, a diluent, and a treated solid oxide.

The terms "a," "an," and "the" are intended to include plural alternatives, e.g., at least one. For instance, the disclosure of "a solid promoter," "a treated solid oxide," or "a diluent," is meant to encompass one, or mixtures or combinations of more than one, solid promoter, treated solid oxide, or diluent, respectively, unless otherwise specified.

Generally, groups of elements are indicated using the numbering scheme indicated in the version of the periodic table of elements published in *Chemical and Engineering News*, 63(5), 27, 1985. In some instances, a group of elements can be indicated using a common name assigned to the group; for example, alkali metals for Group 1 elements, alkaline earth metals for Group 2 elements, transition metals for Group 3-12 elements, and halogens or halides for Group 17 elements.

The term "hydrocarbon" refers to a compound containing only carbon and hydrogen. Other identifiers may be utilized to indicate the presence of particular groups in the hydrocarbon, for instance, a halogenated hydrocarbon indicates the presence of one or more halogen atoms replacing an equivalent number of hydrogen atoms in the hydrocarbon.

As used herein, the term "$\alpha,\beta$-unsaturated carboxylic acid" and its derivatives refer to a carboxylic acid having a carbon atom of a carbon-carbon double bond attached to the carbonyl carbon atom (the carbon atom bearing the double bonded oxygen atom). Optionally, the $\alpha,\beta$-unsaturated carboxylic acid may contain other functional groups and/or heteroatoms.

For any particular compound or group disclosed herein, any name or structure presented is intended to encompass all conformational isomers, regioisomers, stereoisomers, and mixtures thereof that may arise from a particular set of substituents, unless otherwise specified. The name or structure also encompasses all enantiomers, diastereomers, and other optical isomers (if there are any) whether in enantiomeric or racemic forms, as well as mixtures of stereoisomers, as would be recognized by a skilled artisan, unless otherwise specified. For example, a general reference to pentane includes n-pentane, 2-methyl-butane, and 2,2-dimethylpropane; and a general reference to a butyl group includes a n-butyl group, a sec-butyl group, an iso-butyl group, and a t-butyl group.

Various numerical ranges are disclosed herein. When a range of any type is disclosed or claimed, the intent is to disclose or claim individually each possible number that such a range could reasonably encompass, including end points of the range as well as any sub-ranges and combinations of sub-ranges encompassed therein, unless otherwise specified. Moreover, all numerical end points of ranges disclosed herein are approximate. As a representative example, it is disclosed in an aspect of the invention that one or more steps in the processes of this invention can be conducted at a temperature in a range from 10° C. to 75° C. This range should be interpreted as encompassing temperatures in a range from "about" 10° C. to "about" 75° C.

The term "substituted" when used to describe a group, for example, when referring to a substituted analog of a particular group, is intended to describe the compound or group wherein any non-hydrogen moiety formally replaces hydrogen in that group or compound, and is intended to be non-limiting. A compound or group can also be referred to herein as "unsubstituted" or by equivalent terms such as "non-substituted," which refers to the original group or compound. Unless otherwise specific, "substituted" is intended to be non-limiting and include inorganic substituents or organic substituents as specified and as understood by one of ordinary skill in the art.

The terms "contact product," "contacting," and the like, are used herein to describe compositions and methods wherein the components are combined or contacted together in any order, in any manner, and for any length of time, unless otherwise specified. For example, the components can be contacted by blending or mixing. Further, unless otherwise specified, the contacting of any component can occur in the presence or absence of any other component of the compositions and methods described herein. Combining additional materials or components can be done by any suitable method. Further, the term "contact product" includes mixtures, blends, solutions, slurries, reaction products, and the like, or combinations thereof. Although "contact product" can, and often does, include reaction products, it is not required for the respective components to react with one another. Similarly, the term "contacting" is used herein to refer to materials which can be blended, mixed, slurried, dissolved, reacted, treated, or otherwise combined or contacted in some other manner.

Although any methods and materials similar or equivalent to those described herein can be used in the practice or testing of the invention, the typical methods and materials are herein described.

All publications and patents mentioned herein are incorporated herein by reference for the purpose of describing and disclosing, for example, the constructs and methodologies that are described in the publications, which might be used in connection with the presently described invention.

DETAILED DESCRIPTION OF THE INVENTION

The present invention is directed generally to methods for forming $\alpha,\beta$-unsaturated carboxylic acids, or salts thereof. An illustrative example of a suitable $\alpha,\beta$-unsaturated carboxylic acid is acrylic acid.

As disclosed herein, the heterogeneous processes of this invention can provide a distinct advantage over homogeneous systems in the ease of separation (e.g., solid-liquid separation techniques) of the desired reaction product from the solid catalytic promoter (e.g., the treated solid oxide). Moreover, and while not wishing to be bound by the following theory, it is believed that the processes of this invention are also advantageous in that an additional or auxiliary liquid base (e.g., an alkoxide, hydride, or amine) is not needed to perform the disclosed processes. Further, a transition metal complex that is covalently bound or immobilized on a solid support (e.g., with a linking moiety) is not needed to perform the disclosed processes. Further, a heterogeneous base comprising an organic basic moiety that is covalently bound or immobilized on a solid support (e.g., with a linking moiety) is not needed to perform the disclosed processes. Further, a consumable heterogeneous alkalinity reservoir (e.g., NaH) with an organic base dissolved in a reaction media is not needed to perform the disclosed processes. And lastly, an aryloxide (e.g., a fluorophenolate) is not needed to perform the disclosed processes.

Moreover, and while not wishing to be bound by the following theory, it is believed that the combined acid and base functionality (e.g., the combined Lewis acid and Brønsted base characteristics) of certain treated solid oxides disclosed herein may result in the surprisingly high yields in both the metallalactone elimination reactions and the carboxylic acid forming reactions.

Solid Promoters

Generally, the solid promoter used in the processes disclosed herein can comprise (or consist essentially of, or consist of) a solid oxide, a clay or pillared clay, or combinations thereof. For instance, it is contemplated that mixtures or combinations of two or more solid promoters can be employed in certain aspects of the invention. Generally, the term solid promoter is used interchangeably herein with solid activator.

In accordance with one aspect, the solid promoter can comprise a basic promoter, for instance, a solid promoter that can act as a base. Representative and non-limiting examples of basic promoters can include alumina, titania, zirconia, magnesia, boria, calcia, zinc oxide, silica-alumina, silica-coated alumina, silica-titania, silica-zirconia, silica-magnesia, alumina-titania, alumina-zirconia, zinc-aluminate, alumina-boria, silica-boria, aluminum phosphate, aluminophosphate, aluminophosphate-silica, magnesium aluminate, titania-zirconia, and the like, as well as combinations thereof. In accordance with another aspect, the solid promoter can comprise a Lewis acid promoter. Representative and non-limiting examples of Lewis acid promoters can include silica, alumina, titania, zirconia, magnesia, boria, calcia, zinc oxide, silica-alumina, silica-coated alumina, silica-titania, silica-zirconia, silica-magnesia, alumina-titania, alumina-zirconia, zinc-aluminate, alumina-boria, silica-boria, aluminum phosphate, aluminophosphate, aluminophosphate-silica, magnesium aluminate, titania-zirconia, and the like, as well as combinations thereof. In accordance with yet another aspect, the solid promoter can comprise a Brønsted base promoter. Representative and non-limiting examples of Brønsted base promoters can include alumina, titania, zirconia, magnesia, boria, calcia, zinc oxide, silica-coated alumina, silica-titania, silica-zirconia, silica-magnesia, alumina-titania, alumina-zirconia, zinc-aluminate, alumina-boria, silica-boria, aluminum phosphate, aluminophosphate, aluminophosphate-silica, magnesium aluminate, titania-zirconia, and the like, as well as combinations thereof. In accordance with still another aspect, the solid promoter can comprise a Brønsted base and Lewis acid promoter. Representative and non-limiting examples of Brønsted base and Lewis acid promoters can include alumina, titania, zirconia, magnesia, boria, calcia, zinc oxide, silica-coated alumina, silica-titania, silica-zirconia, silica-magnesia, alumina-titania, alumina-zirconia, zinc-aluminate, alumina-boria, silica-boria, aluminum phosphate, aluminophosphate, aluminophosphate-silica, magnesium aluminate, titania-zirconia, and the like, as well as combinations thereof.

Consistent with aspects of this invention, the solid promoter can comprise (or consist essentially of, or consist of) a solid oxide. Generally, the solid oxide can comprise oxygen and one or more elements selected from Group 1, 2, 3, 4, 5, 6, 7, 8, 9, 10, 11, 12, 13, 14, or 15 of the periodic table, or comprise oxygen and one or more elements selected from the lanthanide or actinide elements (See: Hawley's Condensed Chemical Dictionary, 11$^{th}$ Ed., John Wiley & Sons, 1995; Cotton, F. A., Wilkinson, G., Murillo, C. A., and Bochmann, M., Advanced Inorganic Chemistry, 6$^{th}$ Ed., Wiley-Interscience, 1999). For example and not limited thereto, the solid oxide can comprise oxygen and an element, or elements, selected from Al, B, Be, Bi, Cd, Co, Cr, Cu, Fe, Ga, La, Mn, Mo, Ni, Sb, Si, Sn, Sr, Th, Ti, V, W, P, Y, Zn, Zr, Na, K, Cs, Ca, Ba, and Li.

Illustrative examples of solid oxides that can be used as solid promoters as described herein can include, but are not limited to, $Al_2O_3$, $B_2O_3$, BeO, $Bi_2O_3$, BaO, MgO, CaO, CdO, $Ce_2O_3$, $Co_3O_4$, $Cr_2O_3$, CuO, $Fe_2O_3$, $Ga_2O_3$, $K_2O$, $La_2O_3$, $Mn_2O_3$, $MoO_3$, $Na_2O$, NiO, $P_2O_5$, $Sb_2O_5$, $SiO_2$, $SnO_2$, SrO, $ThO_2$, $TiO_2$, $V_2O_5$, $WO_3$, $Y_2O_3$, ZnO, $ZrO_2$, and the like, including mixed oxides thereof, and combinations thereof. In addition, solid oxide is meant to encompass carbonates and hydroxides of the above elements, either alone or in combination. Illustrative and non-limiting examples of carbonates include sodium carbonate, sodium bicarbonate, potassium carbonate, cesium carbonate, and the like.

In an aspect, the solid oxide can comprise silica, alumina, titania, zirconia, magnesia, boria, calcia, zinc oxide, silica-alumina, silica-coated alumina, silica-titania, silica-zirconia, silica-magnesia, alumina-titania, alumina-zirconia, zinc-aluminate, alumina-boria, silica-boria, aluminum phosphate, aluminophosphate, aluminophosphate-silica, magnesium aluminate, titania-zirconia, and the like, or a combination thereof alternatively, silica; alternatively, alumina; alternatively, titania; alternatively, zirconia; alternatively, magnesia; alternatively, boria; alternatively, calcia; alternatively, zinc oxide; alternatively, silica-alumina; alternatively, silica-coated alumina; alternatively, silica-titania; alternatively, silica-zirconia; alternatively, silica-magnesia; alternatively, alumina-titania; alternatively, alumina-zirconia; alternatively, zinc-aluminate; alternatively, alumina-boria; alternatively, silica-boria; alternatively, aluminum phosphate; alternatively, aluminophosphate; alternatively, aluminophosphate-silica; alternatively, magnesium aluminate; or alternatively, titania-zirconia. In another aspect, the solid oxide can comprise magnesium aluminate, calcium aluminate, zinc aluminate, zirconium aluminate, sodium aluminate, magnesium zirconium oxide, sodium zirconium oxide, calcium zirconium oxide, lanthanum chromium oxide, barium titanium oxide, and the like, or a combination thereof; alternatively, magnesium aluminate; alternatively, calcium aluminate; alternatively, zinc aluminate; alternatively, zirconium aluminate; alternatively, sodium aluminate; alternatively, magnesium zirconium oxide; alternatively, sodium zirconium oxide; alternatively, calcium zirconium oxide; alternatively, lanthanum chromium oxide; or alternatively, barium titanium oxide. Various methods for producing suitable solid oxides and mixed solid oxides, such as co-gelling, doping or impregnating are disclosed in, for example, U.S. Pat. Nos. 6,107,230, 6,165,929, 6,294,494, 6,300,271, 6,316,553, 6,355,594, 6,376,415, 6,388,017, 6,391,816, 6,395,666, 6,524,987, 6,548,441, 6,548,442, 6,576,583, 6,613,712, 6,632,894, 6,667,274, 6,750,302, 7,294,599, 7,601,665, 7,884,163, and 8,309,485, which are incorporated herein by reference in their entirety. Other suitable processes and procedures for preparing solid oxides that can be used as solid promoters are well known to those of skill in the art.

As disclosed herein, the solid oxide can comprise silica-coated alumina, as described in U.S. Pat. No. 7,884,163 (e.g., Sasol Siral® 28 or Sasol Siral® 40). Such silica-coated alumina solid oxide materials often are alumina-rich, with the weight ratio of alumina to silica (alumina:silica) in the silica-coated alumina typically falling in a range from 1.05:1 to 50:1, from 1.1:1 to 25:1, from 1.2:1 to 12:1, from 1.2:1 to 4:1, from 1.3:1 to 6:1, or from 1.3:1 to 3:1.

Consistent with aspects of this invention, the solid promoter can comprise (or consist essentially of, or consist of) a clay or a pillared clay. The clay or pillared clay materials that can be employed as a solid promoter in the disclosed processes can encompass clay materials either in their natural state or that have been treated with various ions by wetting, ion exchange, pillaring, or other processes. In some aspects, the clay or pillared clay material can comprise clays that have been ion exchanged with large cations, including polynuclear, highly charged metal complex cations. In other aspects, the clay or pillared clay material can comprise clays that have been ion exchanged with simple salts, including, but not limited to, salts of Al(III), Fe(II), Fe(III), and Zn(II) with ligands such as halide, acetate, sulfate, nitrate, nitrite, and the like.

In another aspect, the clay or pillared clay material can comprise a pillared clay. The term "pillared clay" can be used to refer to clay materials that have been ion exchanged with large, typically polynuclear, highly charged metal complex cations. Examples of such ions include, but are not limited to, Keggin ions which can have charges such as 7+, various polyoxometallates, and other large ions. Thus, the term pillaring generally refers to a simple exchange reaction in which the exchangeable cations of a clay material can be replaced with large, highly charged ions, such as Keggin ions. These polymeric cations are then immobilized within the interlayers of the clay, and when calcined can be converted to metal oxide "pillars," effectively supporting the clay layers as column-like structures. Thus, once the clay has been dried and calcined to produce the supporting pillars between clay layers, the expanded lattice structure can be maintained and the porosity can be enhanced. The resulting pores can vary in shape and size as a function of the pillaring material and the parent clay material used, among other variables. Examples of pillaring and pillared clays are found in: T. J. Pinnavaia, *Science* 220 (4595), 365-371 (1983); J. M. Thomas, Intercalation Chemistry, (S. Whittington and A. Jacobson, eds.) Ch. 3, pp. 55-99, Academic Press, Inc., (1972); U.S. Pat. Nos. 4,452,910; 5,376,611; and 4,060,480; the disclosures of which are incorporated herein by reference in their entirety.

In some aspects, the clay or pillared clay can comprise montmorillonite, bentonite, nontronite, hectorite, halloysite, vermiculite, mica, fluoromica, chlorite, sepiolite, attapulgite, palygorskite, illite, saponite, allophone, smectite, kaolinite, pyrophyllite, and the like, or any combination thereof. In other aspects, the clay or pillared clay can comprise montmorillonite; alternatively, bentonite; alternatively, nontronite; alternatively, hectorite; alternatively, halloysite; alternatively, vermiculite; alternatively, mica; alternatively, fluoromica; alternatively, chlorite; alternatively, sepiolite; alternatively, attapulgite; alternatively, palygorskite; alternatively, illite; alternatively, saponite; alternatively, allophone; alternatively, smectite; alternatively, kaolinite; or alternatively, pyrophyllite.

In accordance with an aspect of this invention, the solid promoter can comprise silica, alumina, silica-alumina, aluminum phosphate, alumina-boria, silica-magnesia, silica-titania, zirconia, magnesia, magnesium aluminate, sepiolite, titania, palygorskite, montmorillonite, talc, kaolinite, halloysite, pyrophyllite, and the like, as well as combinations thereof. In accordance with another aspect, the solid promoter can comprise silica, alumina, silica-alumina, aluminum phosphate, alumina-boria, silica-magnesia, silica-titania, zirconia, magnesia, magnesium aluminate, titania, and the like, as well as combinations thereof. In accordance with yet another aspect, the solid promoter can comprise sepiolite, palygorskite, montmorillonite, talc, kaolinite, halloysite, pyrophyllite, and the like, as well as combinations thereof. In accordance with still another aspect, the solid promoter can comprise alumina, zirconia, magnesia, magnesium aluminate, sepiolite, and the like, as well as combinations thereof; alternatively, alumina; alternatively, zirconia; alternatively, magnesia; alternatively, magnesium aluminate; or alternatively, sepiolite.

The solid promoters contemplated herein can have any suitable surface area, pore volume, and particle size, as would be recognized by those of skill in the art. For instance, the solid promoter can have a pore volume in a range from 0.1 mL/g to 2.5 mL/g, or alternatively, from 0.5 mL/g to 2.5 mL/g. In a further aspect, the promoter can have a pore volume from 1 mL/g to 2.5 mL/g, or from 0.1 mL/g to 1.5 mL/g. Alternatively, the pore volume can be from 0.1 mL/g to 1.0 mL/g, or from 0.2 mL/g to 1.0 mL/g. Additionally, or alternatively, the solid promoter can have a BET surface area in a range from 10 $m^2$/g to 750 $m^2$/g; alternatively, from 100 $m^2$/g to 750 $m^2$/g; alternatively, from 100 $m^2$/g to 500 $m^2$/g; or alternatively, from 30 $m^2$/g to 200 $m^2$/g. In a further aspect, the solid promoter can have a surface area of from 20 $m^2$/g to 500 $m^2$/g, from 30 $m^2$/g to 350 $m^2$/g, from 100 $m^2$/g to 400 $m^2$/g, from 200 $m^2$/g to 450 $m^2$/g, or from 150 $m^2$/g to 350 $m^2$/g. The average particle size of the solid promoter can vary greatly depending upon the process specifics, however, average particle sizes in the range of from 5 microns to 500 microns, from 10 microns to 250 microns, or from 25 microns to 200 microns, are often employed. Alternatively, ⅛ inch to ¼ inch pellets or beads can be used.

Prior to use, these solid promoters can be calcined. The calcining step can be conducted at a variety of temperatures and time periods, and in a variety of atmospheres (an inert atmosphere, an oxidizing atmosphere, a reducing atmosphere). For instance, the calcining step can be conducted at a peak calcining temperature in a range from 150° C. to 1000° C.; alternatively, from 250° C. to 1000° C.; alternatively, from 200° C. to 750° C.; alternatively, from 200° C. to 600° C.; alternatively, from 250° C. to 950° C.; alternatively, from 250° C. to 750° C.; alternatively, from 400° C. to 700° C.; alternatively, from 300° C. to 650° C.; or alternatively, from 400° C. to 600° C. In these and other aspects, these temperature ranges also are meant to encompass circumstances where the calcining step is conducted at a series of different temperatures (e.g., an initial calcining temperature, a peak calcining temperature), instead of at a single fixed temperature, falling within the respective ranges. For instance, the calcining step can start at an initial calcining temperature, and subsequently, the temperature of the calcining step can be increased to the peak calcining temperature, for example, a peak calcining temperature in a range from 500° C. to 1000° C., or from 250° C. to 750° C.

The duration of the calcining step is not limited to any particular period of time. Hence, the calcining step can be conducted, for example, in a time period ranging from as little as 15-45 minutes to as long as 12-24 hours, or more. The appropriate calcining time can depend upon, for example, the initial/peak calcining temperature, and the atmosphere under which calcining is conducted, among other variables. Generally, however, the calcining step can be conducted in a time period that can be in a range from 45 minutes to 18 hours, such as, for example, from 45 minutes to 15 hours, from 1 hour to 12 hours, from 2 hours to 10 hours, from 3 hours to 10 hours, or from 4 hours to 10 hours.

In accordance with the present invention, the solid promoter can comprise (or consist essentially of, or consist of) a treated solid oxide. For example, the treated solid oxide can be a calcined solid oxide, a metal-treated solid oxide, a metal-treated chemically-modified solid oxide, or a combination thereof. The solid oxide of the treated solid oxide can be any suitable solid oxide, or any solid oxide disclosed herein, such as alumina, silica-alumina, silica-coated alumina, aluminophosphate, sodium carbonate, or sodium bicarbonate, and the like. Combinations of more than one treated solid oxide, if desired, can be used in the processes of this invention. In a particular aspect of this invention, the solid oxide can comprise alumina, silica-alumina, silica-coated alumina, or a mixture thereof.

Consistent with aspects of this invention, the treated solid oxide can be characterized as a Lewis acid. Additionally or alternatively, the treated solid oxide can be characterized as a Brønsted base. Accordingly, in some aspects, the treated solid oxide can be characterized as both a Brønsted base and a Lewis acid.

As disclosed herein, the treated solid oxide can be a calcined solid oxide. Generally, prior to step (1) or step (I) of the processes of this invention, the treated solid oxide can be formed by calcining at any suitable temperature, or at a temperature in any range disclosed herein. Calcining temperatures in a range from 150° C. to 1000° C., from 200° C. to 750° C., or from 200° C. to 600° C., often can be used. Illustrative and non-limiting examples of treated solid oxides in this aspect of the invention can include calcined sodium carbonate, calcined sodium bicarbonate, calcined potassium carbonate, calcined cesium carbonate, calcined alumina, calcined zirconia, calcined magnesia, and the like, as well as combinations thereof.

As disclosed herein, the treated solid oxide can be a metal-treated solid oxide. The term "metal-treated" solid oxide is meant to encompass solid oxides that may be described alternatively as one or more of metal-containing solid oxides, metal-impregnated solid oxides, metal-modified solid oxides, and/or metal-enriched solid oxides. Generally, prior to step (1) or step (I) of the processes of this invention, the metal-treated solid oxide can be produced by a process comprising contacting any suitable solid oxide and any suitable metal-containing compound and calcining. The calcining can be performed concurrently with this contacting step and/or subsequent to this contacting step, and can be performed at any suitable conditions or at any calcining conditions disclosed herein.

The metal-treated solid oxide can comprise an alkali metal, an alkaline earth metal, a transition metal, or any combination thereof (e.g., a transition metal and an alkali metal). When the metal-treated solid oxide comprises an alkali metal, the treated solid oxide can be referred to as an alkali metal-treated solid oxide, and the alkali metal often comprises sodium, potassium, or cesium, either singly or in combination. Illustrative and non-limiting examples of alkali-metal treated solid oxides can include sodium-treated alumina, potassium-treated alumina, cesium-treated alumina, sodium-treated aluminophosphate, and the like, as well as combinations thereof. When the metal-treated solid oxide comprises an alkaline earth metal, the treated solid oxide can be referred to as an alkaline earth metal-treated solid oxide, and the alkaline earth metal often comprises magnesium, calcium, or barium, either singly or in combination. Illustrative and non-limiting examples of alkaline earth metal-treated solid oxides can include magnesium-treated alumina, calcium-treated alumina, barium-treated alumina, and the like, as well as combinations thereof. When the metal-treated solid oxide comprises a transition metal, the treated solid oxide can be referred to as a transition metal-treated solid oxide, and the transition metal can comprise any transition metal disclosed herein, such as titanium, zirconium, hafnium, tungsten, or zinc, and either singly or in combination. Illustrative and non-limiting examples of transition metal-treated solid oxides can include zinc-treated alumina, zirconium-treated alumina, sodium-tungsten-treated alumina, and the like, as well as combinations thereof.

As disclosed herein, the treated solid oxide can be a metal-treated chemically-modified solid oxide. Generally, prior to step (1) or step (I) of the processes of this invention, the metal-treated chemically-modified solid oxide can be produced by a process comprising contacting any suitable solid oxide and any electron-withdrawing anion and calcining (concurrently and/or subsequently) to form the chemically-modified solid oxide, and then contacting the chemically-modified solid oxide with any suitable metal-containing compound. Optionally, a further calcining step can be used.

The metal-treated chemically-modified solid oxide can comprise an alkali metal, an alkaline earth metal, a transition metal, or any combination thereof (e.g., a transition metal and an alkali metal). When the metal-treated chemically-modified solid oxide comprises an alkali metal, the treated solid oxide can be referred to as an alkali metal-treated chemically-modified solid oxide, and the alkali metal often comprises sodium, potassium, or cesium, either singly or in combination. When the metal-treated chemically-modified solid oxide comprises an alkaline earth metal, the treated solid oxide can be referred to as an alkaline earth metal-treated chemically-modified solid oxide, and the alkaline earth metal often comprises magnesium, calcium, or barium, either singly or in combination. When the metal-treated chemically-modified solid oxide comprises a transition metal, the treated solid oxide can be referred to as a transition metal-treated chemically-modified solid oxide, and the transition metal can comprise any transition metal disclosed herein, such as titanium, zirconium, hafnium, tungsten, or zinc, and either singly or in combination. Illustrative and non-limiting examples of metal-treated chemically-modified solid oxides can include sodium-treated chlorided alumina, sodium-treated sulfated alumina, sodium-treated sulfated silica-coated alumina, sodium-treated fluorided silica-coated alumina, sodium-treated fluorided silica-alumina, sodium-treated fluorided-chlorided silica-coated alumina, and the like, as well as combinations thereof.

When present, any metal in a metal-treated solid oxide or a metal-treated chemically-modified solid oxide often is present in an amount of at least 0.5 wt. %, or at least 1 wt. %. For instance, the metal-treated solid oxide (or metal-treated chemically-modified solid oxide) generally can contain from 1 to 30 wt. % of the metal, based on the weight of the metal-treated solid oxide (or metal-treated chemically-modified solid oxide). In particular aspects provided herein, the metal-treated solid oxide (or metal-treated chemically-modified solid oxide) can contain from 1 to 25 wt. %, from 2 to 30 wt. %, from 2 to 25 wt. %, from 5 to 30 wt. %, from 5 to 25 wt. %, from 3 to 15 wt. %, from 5 to 12 wt. %, or from 6 to 18 wt. %, of the metal, based on the total weight of the metal-treated solid oxide (or metal-treated chemically-modified solid oxide).

In the processes disclosed herein, any suitable chemically-modified solid oxide can be employed in this invention, whether one chemically-modified solid oxide or a mixture or combination of two or more different chemically-modified solid oxides. The chemically-modified solid oxide can comprise a solid oxide contacted with an electron-withdrawing anion, for instance, any solid oxide and any electron-withdrawing anion disclosed herein. In an aspect, the chemically-modified solid oxide can comprise a solid oxide contacted with an electron-withdrawing anion, the solid oxide containing a Lewis-acidic metal ion. Non-limiting examples of suitable chemically-modified solid oxides are disclosed in, for instance, U.S. Pat. Nos. 7,294,599, 7,601,665, 7,884,163, 8,309,485, 8,623,973, 8,703,886, and 9,023,959, incorporated herein by reference in their entirety.

The electron-withdrawing component used to treat or modify the solid oxide can be any component that can increase the Lewis or Brønsted acidity of the solid oxide upon treatment (as compared to the solid oxide that is not treated with at least one electron-withdrawing anion). According to one aspect, the electron-withdrawing component can be an electron-withdrawing anion derived from a salt, an acid, or other compound, such as a volatile organic compound, that serves as a source or precursor for that anion. Examples of electron-withdrawing anions can include, but are not limited to, sulfate, bisulfate, fluoride, chloride, bromide, iodide, fluorosulfate, fluoroborate, phosphate, fluorophosphate, trifluoroacetate, triflate, fluorozirconate, fluorotitanate, phospho-tungstate, tungstate, and molybdate, including mixtures and combinations thereof. In addition, other ionic or non-ionic compounds that serve as sources for these electron-withdrawing anions also can be employed. It is contemplated that the electron-withdrawing anion can be, or can comprise, fluoride, chloride, bromide, phosphate, triflate, bisulfate, or sulfate, or any combination thereof, in some aspects provided herein. In other aspects, the electron-withdrawing anion can comprise sulfate, bisulfate, fluoride, chloride, bromide, iodide, fluorosulfate, fluoroborate, phosphate, fluorophosphate, trifluoroacetate, triflate, fluorozirconate, fluorotitanate, or combinations thereof. Yet, in other aspects, the electron-withdrawing anion can comprise sulfate, fluoride, chloride, or combinations thereof alternatively, sulfate; alternatively, fluoride and chloride; or alternatively, fluoride.

The chemically-modified solid oxide generally can contain from 1 to 30 wt. % of the electron-withdrawing anion, based on the weight of the chemically-modified solid oxide. In particular aspects provided herein, the chemically-modified solid oxide can contain from 1 to 20 wt. %, from 2 to 20 wt. %, from 3 to 20 wt. %, from 2 to 15 wt. %, from 3 to 15 wt. %, from 3 to 12 wt. %, from 4 to 10 wt. %, or from 5 to 9 wt. %, of the electron-withdrawing anion, based on the total weight of the chemically-modified solid oxide.

In one aspect, the chemically-modified solid oxide can comprise fluorided alumina, chlorided alumina, bromided alumina, sulfated alumina, fluorided silica-alumina, chlorided silica-alumina, bromided silica-alumina, sulfated silica-alumina, fluorided silica-zirconia, chlorided silica-zirconia, bromided silica-zirconia, sulfated silica-zirconia, fluorided silica-titania, fluorided silica-coated alumina, fluorided-chlorided silica-coated alumina, sulfated silica-coated alumina, or phosphated silica-coated alumina, as well as any mixture or combination thereof. In another aspect, the chemically-modified solid oxide employed in the processes described herein can be, or can comprise, a fluorided solid oxide and/or a sulfated solid oxide, non-limiting examples of which can include fluorided alumina, sulfated alumina, fluorided silica-alumina, sulfated silica-alumina, fluorided silica-zirconia, fluorided silica-coated alumina, fluorided-chlorided silica-coated alumina, or sulfated silica-coated alumina, as well as combinations thereof. In yet another aspect, the chemically-modified solid oxide can comprise fluorided alumina; alternatively, chlorided alumina; alternatively, sulfated alumina; alternatively, fluorided silica-alumina; alternatively, sulfated silica-alumina; alternatively, fluorided silica-zirconia; alternatively, chlorided silica-zirconia; alternatively, sulfated silica-coated alumina; alternatively, fluorided-chlorided silica-coated alumina; or alternatively, fluorided silica-coated alumina. In some aspect, the chemically-modified solid oxide can comprise a fluorided solid oxide, while in other aspects, the chemically-modified solid oxide can comprise a sulfated solid oxide.

Various processes can be used to form chemically-modified solid oxides useful in the present invention. Methods of contacting the solid oxide with the electron-withdrawing component, suitable electron withdrawing components and addition amounts, impregnation with metals or metal ions (e.g., zinc, nickel, vanadium, titanium, silver, copper, gallium, tin, tungsten, molybdenum, zirconium, or combinations thereof), various calcining procedures and conditions (e.g., calcining temperatures in a range from 150° C. to 1000° C., from 200° C. to 750° C., or from 400° C. to 700° C.), calcination times (e.g., calcination times in a range from 1 minute to 24 hours, from 5 minutes to 10 hours, or from 20 minutes to 6 hours), calcination equipment (e.g., calcination equipment such as a rotary kiln, muffle furnace, or fluidized bed, among other methods of conveying heat), and calcination atmospheres (e.g., dry or humid calcination atmospheres, oxidizing calcination atmospheres such as air or oxygen, reducing calcination atmospheres such as carbon monoxide or hydrogen, or non-reactive calcination atmospheres like nitrogen or argon) are disclosed in, for example, U.S. Pat. Nos. 6,107,230, 6,165,929, 6,294,494, 6,300,271, 6,316,553, 6,355,594, 6,376,415, 6,388,017, 6,391,816, 6,395,666, 6,524,987, 6,548,441, 6,548,442, 6,576,583, 6,613,712, 6,632,894, 6,667,274, 6,750,302, 7,294,599, 7,601,665, 7,884,163, and 8,309,485, which are incorporated herein by reference in their entirety. Other suitable processes and procedures for preparing chemically-modified solid oxides (e.g., sulfated alumina, fluorided silica-alumina, and fluorided silica-coated alumina, among others) are well known to those of skill in the art.

Diluents

The processes disclosed herein typically are conducted in the presence of a diluent. Mixtures and/or combinations of diluents can be utilized in these processes. The diluent can comprise, consist essentially of, or consist of, any suitable solvent or any solvent disclosed herein, unless otherwise specified. For instance, in accordance with one aspect of this invention, the diluent can comprise a non-protic solvent. Representative and non-limiting examples of non-protic solvents can include tetrahydrofuran (THF), 2,5-Me$_2$THF, acetone, toluene, chlorobenzene, pyridine, carbon dioxide, and the like, as well as combinations thereof. In accordance with another aspect, the diluent can comprise a weakly coordinating or non-coordinating solvent. Representative and non-limiting examples of weakly coordinating or non-coordinating solvents can include toluene, chlorobenzene, paraffins, halogenated paraffins, and the like, as well as combinations thereof. In accordance with yet another aspect, the diluent can comprise a carbonyl-containing solvent, for instance, ketones, esters, amides, and the like, as well as combinations thereof. Representative and non-limiting examples of carbonyl-containing solvents can include acetone, ethyl methyl ketone, ethyl acetate, propyl acetate, butyl acetate, isobutyl isobutyrate, methyl lactate, ethyl lactate, N,N-dimethylformamide, and the like, as well as combinations thereof. In still another aspect, the diluent can comprise THF, 2,5-Me$_2$THF, methanol, acetone, toluene, chlorobenzene, pyridine, or a combination thereof; alternatively, THF; alternatively, 2,5-Me$_2$THF; alternatively, methanol; alternatively, acetone; alternatively, toluene; alternatively, chlorobenzene; or alternatively, pyridine.

In an aspect, the diluent can comprise (or consist essentially of, or consist of) an aromatic hydrocarbon solvent. Non-limiting examples of suitable aromatic hydrocarbon solvents that can be utilized singly or in any combination include benzene, toluene, xylene (inclusive of ortho-xylene, meta-xylene, para-xylene, or mixtures thereof), and ethylbenzene, or combinations thereof; alternatively, benzene; alternatively, toluene; alternatively, xylene; or alternatively, ethylbenzene.

In an aspect, the diluent can comprise (or consist essentially of, or consist of) a halogenated aromatic hydrocarbon solvent. Non-limiting examples of suitable halogenated aromatic hydrocarbon solvents that can be utilized singly or in any combination include chlorobenzene, dichlorobenzene, and combinations thereof alternatively, chlorobenzene; or alternatively, dichlorobenzene.

In an aspect, the diluent can comprise (or consist essentially of, or consist of) an ether solvent. Non-limiting examples of suitable ether solvents that can be utilized singly or in any combination include dimethyl ether, diethyl ether, diisopropyl ether, di-n-propyl ether, di-n-butyl ether, diphenyl ether, methyl ethyl ether, methyl t-butyl ether, dihydrofuran, tetrahydrofuran (THF), 2,5-Me$_2$THF, 1,2-dimethoxyethane, 1,4-dioxane, and combinations thereof; alternatively, diethyl ether, dibutyl ether, THF, 2,5-Me$_2$THF, 1,2-dimethoxyethane, 1,4-dioxane, and combinations thereof; alternatively, THF; or alternatively, diethyl ether.

Metallalactones and Transition Metal-Ligand Complexes

Generally, the processes disclosed herein employ a metallalactone or a transition metal-ligand complex. The transition metal of the metallalactone, or of the transition metal-ligand complex, can be a Group 3 to Group 8 transition metal or, alternatively, a Group 8 to Group 11 transition metal. In one aspect, for instance, the transition metal can be Fe, Co, Ni, Cu, Ru, Rh, Pd, Ag, Ir, Pt, or Au, while in another aspect, the transition metal can be Fe, Ni, or Rh. Alternatively, the transition metal can be Fe; alternatively, the transition metal can be Co; alternatively, the transition metal can be Ni; alternatively, the transition metal can be Cu; alternatively, the transition metal can be Ru; alternatively, the transition metal can be Rh; alternatively, the transition metal can be Pd; alternatively, the transition metal can be Ag; alternatively, the transition metal can be Ir; alternatively, the transition metal can be Pt; or alternatively, the transition metal can be Au.

In particular aspects contemplated herein, the transition metal can be Ni. Hence, the metallalactone can be a nickelalactone and the transition metal-ligand complex can be a Ni-ligand complex in these aspects.

The ligand of the metallalactone, or of the transition metal-ligand complex, can be any suitable neutral electron donor group and/or Lewis base. For instance, the suitable neutral ligands can include sigma-donor solvents that contain a coordinating atom (or atoms) that can coordinate to the transition metal of the metallalactone (or of the transition metal-ligand complex). Examples of suitable coordinating atoms in the ligands can include, but are not limited to, O, N, S, and P, or combinations of these atoms. In some aspects consistent with this invention, the ligand can be a bidentate ligand.

In an aspect, the ligand used to form the metallalactone or the transition metal-ligand complex can be an ether, an organic carbonyl, a thioether, an amine, a nitrile, or a phosphine. In another aspect, the ligand used to form the metallalactone or the transition metal-ligand complex can be an acyclic ether, a cyclic ether, an acyclic organic carbonyl, a cyclic organic carbonyl, an acyclic thioether, a cyclic thioether, a nitrile, an acyclic amine, a cyclic amine, an acyclic phosphine, or a cyclic phosphine.

Suitable ethers can include, but are not limited to, dimethyl ether, diethyl ether, dipropyl ether, dibutyl ether, methyl ethyl ether, methyl propyl ether, methyl butyl ether, diphenyl ether, ditolyl ether, tetrahydrofuran, 2-methyltetrahydrofuran, 2,5-dimethyltetrahydrofuran, 2,3-dihydrofuran, 2,5-dihydrofuran, furan, benzofuran, isobenzofuran, dibenzofuran, tetrahydropyran, 3,4-dihydro-2H-pyran, 3,6-dihydro-2H-pyran, 2H-pyran, 4H-pyran, 1,3-dioxane, 1,4-dioxane, morpholine, and the like, including substituted derivatives thereof.

Suitable organic carbonyls can include ketones, aldehydes, esters, and amides, either alone or in combination, and illustrative examples can include, but are not limited to, acetone, acetophonone, benzophenone, N,N-dimethylformamide, N,N-dimethylacetamide, methyl acetate, ethyl acetate, and the like, including substituted derivatives thereof.

Suitable thioethers can include, but are not limited to, dimethyl thioether, diethyl thioether, dipropyl thioether, dibutyl thioether, methyl ethyl thioether, methyl propyl thioether, methyl butyl thioether, diphenyl thioether, ditolyl thioether, thiophene, benzothiophene, tetrahydrothiophene, thiane, and the like, including substituted derivatives thereof.

Suitable nitriles can include, but are not limited to, acetonitrile, propionitrile, butyronitrile, benzonitrile, 4-methylbenzonitrile, and the like, including substituted derivatives thereof.

Suitable amines can include, but are not limited to, methyl amine, ethyl amine, propyl amine, butyl amine, dimethyl amine, diethyl amine, dipropyl amine, dibutyl amine, trimethyl amine, triethyl amine, tripropyl amine, tributyl amine, aniline, diphenylamine, triphenylamine, tolylamine, xylylamine, ditolylamine, pyridine, quinoline, pyrrole, indole, 2-methylpyridine, 3-methylpyridine, 4-methylpyridine, 2,5-dimethylpyrrole, 2,5-diethylpyrrole, 2,5-dipropylpyrrole, 2,5-dibutylpyrrole, 2,4-dimethylpyrrole, 2,4-diethylpyrrole, 2,4-dipropylpyrrole, 2,4-dibutylpyrrole, 3,4-dimethylpyrrole, 3,4-diethylpyrrole, 3,4-dipropylpyrrole, 3,4-dibutylpyrrole, 2-methylpyrrole, 2-ethylpyrrole, 2-propylpyrrole, 2-butylpyrrole, 3-methylpyrrole, 3-ethylpyrrole, 3-propylpyrrole, 3-butylpyrrole, 3-ethyl-2,4-dimethylpyrrole, 2,3,4,5-tetramethylpyrrole, 2,3,4,5-tetraethylpyrrole, 2,2'-bipyridine, 1, 8-diazabicyclo[5.4.0]undec-7-ene, di(2-pyridyl)dimethylsilane, N,N,N',N'-tetramethylethylenediamine, 1,10-phenanthroline, 2, 9-dimethyl-1,10-phenanthroline, glyoxal-bis(mesityl)-1,2-diimine and the like, including substituted derivatives thereof. Suitable amines can be primary amines, secondary amines, or tertiary amines.

Suitable phosphines and other phosphorus compounds can include, but are not limited to, trimethylphosphine, triethylphosphine, tripropylphosphine, tributylphosphine, phenylphosphine, tolylphosphine, diphenylphosphine, ditolylphosphine, triphenylphosphine, tritolylphosphine, methyldiphenylphosphine, dimethylphenylphosphine, ethyldiphenylphosphine, diethylphenylphosphine, tricyclohexylphosphine, trimethyl phosphite, triethyl phosphite, tripropyl phosphite, triisopropyl phosphite, tributyl phosphite and tricyclohexyl phosphite, 2-(di-t-butylphosphino)biphenyl, 2-di-t-butylphosphino-1,1'-binaphthyl, 2-(di-t-butylphosphino)-3,6-dimethoxy-2',4',6'-tri-i-propyl-1,1'-biphenyl, 2-di-t-butylphosphino-2'-methylbiphenyl, 2-(di-t-butylphosphinomethyl)pyridine, 2-di-t-butylphosphino-2',4',6'-tri-i-propyl-1,1'-biphenyl, 2-(dicyclohexylphosphino)biphenyl, (S)-(+)-(3,5-dioxa-4-phospha-cyclohepta[2,1-a;3,4-a'] dinaphthalen-4-yl)dimethylamine, 2-(diphenylphosphino)-2'-methoxy-1,1'-binaphthyl, 1,2,3,4,5-pentaphenyl-1'-(di-t-butylphosphino)ferrocene, 2,2'-bis(diphenylphosphino)-1, 1'-binaphthyl (BINAP), 1,2-bis(dimethylphosphino)ethane, 1,2-bis(diethylphosphino)ethane, 1,2-bis(dipropylphosphino)-ethane, 1,2-bis(diisopropylphosphino)ethane, 1,2-bis(dibutyl-phosphino)ethane, 1,2-bis(di-t-butyl-phosphino) ethane, 1,2-bis(dicyclohexylphosphino)ethane, 1,3-bis(dicyclohexylphosphino)propane, 1,3-bis(diisopropylphosphino)propane, 1,3-bis(diphenylphosphino)propane, 1,3-bis(di-t-butylphosphino)propane, 1,4-bis(diisopropylphosphino)butane, 1,4-bis(diphenylphosphino)butane, 2,2'-bis[bis(3,5-dimethylphenyl)phosphino]-4,4',6, 6'-tetramethoxybiphenyl, 2,6-bis(di-t-butylphosphinomethyl)pyridine, 2,2'-bis(dicyclohexylphosphino)-1,1'-biphenyl, bis(2-dicyclohexylphosphinophenyl)ether, 5,5'-bis(diphenylphosphino)-4,4'-bi-1,3-benzodioxole, 2-t-butylphosphinomethylpyridine, bis(diphenylphosphino) ferrocene, bis(diphenylphosphino)methane, bis (dicyclohexylphosphino)methane, bis(di-t-butylphosphino) methane, and the like, including substituted derivatives thereof.

In other aspects, the ligand used to form the metallalactone or the transition metal-ligand complex can be a carbene, for example, a N-heterocyclic carbene (NHC) compound. Representative and non-limiting examples of suitable N-heterocyclic carbene (NHC) materials include the following:

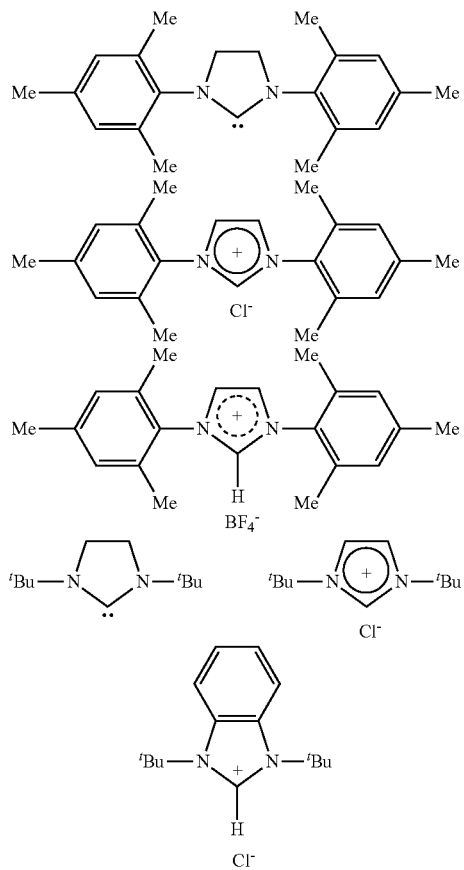

Illustrative and non-limiting examples of metallalactone complexes (representative nickelalactones) suitable for use as described herein include the following compounds (Cy=cyclohexyl, $^tBu$=tert-butyl):

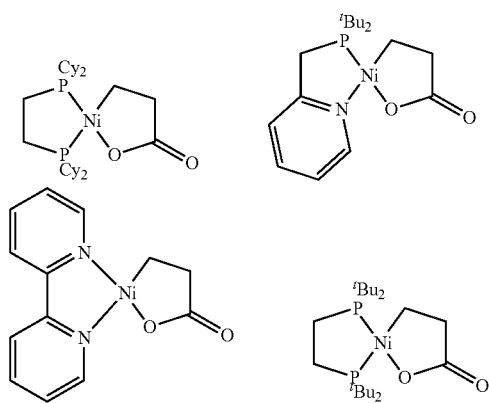

The transition metal-ligand complexes corresponding to these illustrative metallalactones are shown below:

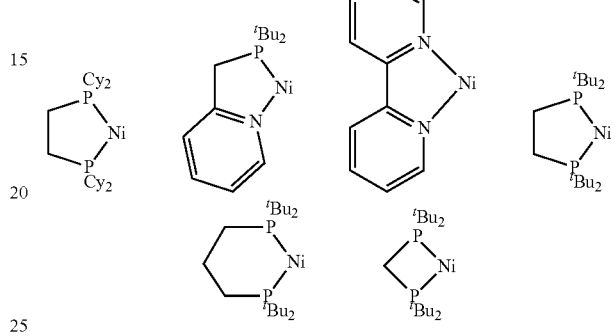

Metallalactones can be synthesized according to the following general reaction scheme (illustrated with nickel as the transition metal; $Ni(COD)_2$ is bis(1,5-cyclooctadiene)nickel(0)):

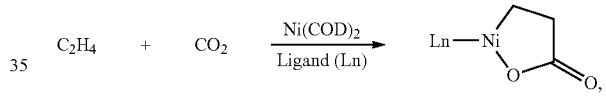

and according to suitable procedures well known to those of skill in the art.

Suitable ligands, transition metal-ligand complexes, and metallalactones are not limited solely to those ligands, transition metal-ligand complexes, and metallalactones disclosed herein. Other suitable ligands, transition metal-ligand complexes, and/or metallalactones are described, for example, in U.S. Pat. Nos. 7,250,510, 8,642,803, and 8,697,909; WO 2015/173276; WO 2015/173277; Journal of Organometallic Chemistry, 1983, 251, C51-C53; Z. Anorg. Allg. Chem., 1989, 577, 111-114; Journal of Organometallic Chemistry, 2004, 689, 2952-2962; Organometallics, 2004, Vol. 23, 5252-5259; Chem. Commun., 2006, 2510-2512; Organometallics, 2010, Vol. 29, 2199-2202; Chem. Eur. J., 2012, 18, 14017-14025; Organometallics, 2013, 32 (7), 2152-2159; and Chem. Eur. J., 2014, Vol. 20, 11, 3205-3211; the disclosures of which are incorporated herein by reference in their entirety.

Producing α,β-Unsaturated Carboxylic Acids and Salts Thereof

Generally, the features of the processes disclosed herein (e.g., the metallalactone, the diluent, the solid promoter (e.g., the treated solid oxide), the α,β-unsaturated carboxylic acid or salt thereof, the transition metal-ligand complex, the olefin, and the conditions under which the α,β-unsaturated carboxylic acid, or a salt thereof, is formed, among others) are independently described, and these features may be combined in any combination to further describe the disclosed processes.

In accordance with an aspect of the present invention, a process for performing a metallalactone elimination reaction is disclosed. This process can comprise (or consist essentially of, or consist of):
(1) contacting
  (a) a metallalactone;
  (b) a diluent; and
  (c) a solid promoter (e.g., a treated solid oxide); and
(2) forming an α,β-unsaturated carboxylic acid, or a salt thereof.

Suitable metallalactones, diluents, and solid promoters (e.g., treated solid oxides) are disclosed hereinabove. In this process for performing a metallalactone elimination reaction, for instance, at least a portion of the diluent can comprise the α,β-unsaturated carboxylic acid, or the salt thereof, that is formed in step (2) of this process.

In accordance with another aspect of the present invention, a process for producing an α,β-unsaturated carboxylic acid, or a salt thereof, is disclosed. This process can comprise (or consist essentially of, or consist of):
(1) contacting
  (a) a metallalactone;
  (b) a diluent; and
  (c) a solid promoter (e.g., a treated solid oxide);
(2) forming an adduct of an α,β-unsaturated carboxylic acid adsorbed onto the solid promoter; and
(3) treating the adduct adsorbed onto the solid promoter to produce the α,β-unsaturated carboxylic acid, or the salt thereof.

In this process for producing an α,β-unsaturated carboxylic acid or a salt thereof, for instance, at least a portion of the diluent comprising a transition metal of the metallalactone can be removed after step (2), and before step (3), of this process. Suitable metallalactones, diluents, and solid promoters (e.g., treated solid oxides) are disclosed hereinabove.

In some aspects, the contacting step—step (1)—of these processes can include contacting, in any order, the metallalactone, the diluent, and the solid promoter (e.g., the treated solid oxide), and additional unrecited materials. In other aspects, the contacting step can consist essentially of, or consist of, the metallalactone, the diluent, and the solid promoter (e.g., the treated solid oxide) components. Likewise, additional materials or features can be employed in the forming step—step (2)—of these processes, and/or in the treating step—step (3)—of the process for producing the α,β-unsaturated carboxylic acid, or the salt thereof. Further, it is contemplated that these processes for performing a metallalactone elimination reaction and for producing an α,β-unsaturated carboxylic acid, or a salt thereof, can employ more than one metallalactone and/or more than one solid promoter (e.g., a mixture of two treated solid oxides). Additionally, a mixture or combination of two or more diluents can be employed, if desired.

Any suitable reactor, vessel, or container can be used to contact the metallalactone, diluent, and solid promoter (e.g., treated solid oxide), non-limiting examples of which can include a flow reactor, a continuous reactor, a fixed bed reactor, and a stirred tank reactor, including more than one reactor in series or in parallel, and including any combination of reactor types and arrangements. In particular aspects consistent with this invention, the metallalactone and the diluent contact a fixed bed of the solid promoter (e.g., the treated solid oxide), for instance, in a suitable vessel, such as in a continuous fixed bed reactor. In further aspects, combinations of more than one solid promoter can be used, such as a mixed bed of a first treated solid oxide and a second treated solid oxide, or sequential beds of a first treated solid oxide and a second treated solid oxide. In these and other aspects, the feed stream can flow upward or downward through the fixed bed. For instance, the metallalactone and the diluent can contact the first treated solid oxide and then the second treated solid oxide in a downward flow orientation, and the reverse in an upward flow orientation. In a different aspect, the metallalactone and the solid promoter (e.g., the treated solid oxide) can be contacted by mixing or stirring in the diluent, for instance, in a suitable vessel, such as a stirred tank reactor.

Step (2) of the process for producing an α,β-unsaturated carboxylic acid, or a salt thereof, recites forming an adduct of the α,β-unsaturated carboxylic acid adsorbed onto the solid promoter (e.g., the treated solid oxide). This adduct can contain all or a portion of the α,β-unsaturated carboxylic acid, and is inclusive of salts of the α,β-unsaturated carboxylic acid.

In step (3) of the process for producing an α,β-unsaturated carboxylic acid or a salt thereof, the adduct adsorbed onto the solid promoter (e.g., the treated solid oxide) is treated to produce the α,β-unsaturated carboxylic acid, or the salt thereof. Various methods can be used to liberate or desorb the α,β-unsaturated carboxylic acid, or the salt thereof, from the solid promoter (e.g., the treated solid oxide). In one aspect, for instance, the treating step can comprise contacting the adduct adsorbed onto the solid promoter (e.g., the treated solid oxide) with an acid. Representative and non-limiting examples of suitable acids can include HCl, acetic acid, sodium bisulfate, and the like, as well as combinations thereof. In another aspect, the treating step can comprise contacting the adduct adsorbed onto the solid promoter (e.g., the treated solid oxide) with a base. Representative and non-limiting examples of suitable bases can include carbonates (e.g., $Na_2CO_3$, $Cs_2CO_3$, $MgCO_3$), hydroxides (e.g., $Mg(OH)_2$, $Na(OH)$), alkoxides (e.g., $Al(O^iPr)_3$, $Na(O^tBu)$, $Mg(OEt)_2$), and the like, as well as combinations thereof ($^iPr$=isopropyl, $^tBu$=tert-butyl, Et=ethyl). In yet another aspect, the treating step can comprise contacting the adduct adsorbed onto the solid promoter (e.g., the treated solid oxide) with a suitable solvent. Representative and non-limiting examples of suitable solvents can include carbonyl-containing solvents such as ketones, esters, or amides (e.g., acetone, ethyl acetate, or N,N-dimethylformamide, as described herein above), alcohol solvents, water, and the like, as well as combinations thereof. In still another aspect, the treating step can comprise heating the adduct adsorbed onto the solid promoter (e.g., the treated solid oxide) to any suitable temperature. This temperature can be in a range, for example, from 50° C. to 1000° C., from 100° C. to 800° C., from 150° C. to 600° C., from 250° C. to 1000° C., from 250° C. to 550° C., or from 150° C. to 500° C. The duration of this heating step is not limited to any particular period of time, as long of the period of time is sufficient to liberate the α,β-unsaturated carboxylic acid from the solid promoter (e.g., the treated solid oxide). As those of skill in the art recognize, the appropriate treating step depends upon several factors, such as the particular diluent used in the process, and the particular solid promoter (e.g., treated solid oxide) used in the process, amongst other considerations.

In these processes for performing a metallalactone elimination reaction and for producing an α,β-unsaturated carboxylic acid (or a salt thereof), additional process steps can be conducted before, during, and/or after any of the steps described herein. As an example, these processes can further comprise a step (e.g., prior to step (1)) of contacting a transition metal-ligand complex with an olefin and carbon dioxide ($CO_2$) to form the metallalactone. Transition metal-ligand complexes are described hereinabove. Illustrative and non-limiting examples of suitable olefins can include ethylene, propylene, butene (e.g., 1-butene), pentene, hexene (e.g., 1-hexene), heptene, octene (e.g., 1-octene), styrene, and the like, as well as combinations thereof.

Yet, in accordance with another aspect of the present invention, a process for producing an α,β-unsaturated carboxylic acid, or a salt thereof, is disclosed. This process can comprise (or consist essentially of, or consist of):
(I) contacting
  (i) a transition metal-ligand complex;
  (ii) an olefin;
  (iii) carbon dioxide ($CO_2$);
  (iv) a diluent; and
  (v) a solid promoter (e.g., a treated solid oxide); and
(II) forming the α,β-unsaturated carboxylic acid, or the salt thereof.

Suitable transition metal-ligands, olefins, diluents, and solid promoters (e.g., treated solid oxides) are disclosed hereinabove. In some aspects, the contacting step—step (I)—of this process can include contacting, in any order, the transition metal-ligand, the olefin, the diluent, the solid promoter (e.g., the treated solid oxide), and carbon dioxide, and additional unrecited materials. In other aspects, the contacting step can consist essentially of, or consist of, contacting, in any order, the transition metal-ligand, the olefin, the diluent, the solid promoter (e.g., the treated solid oxide), and carbon dioxide. Likewise, additional materials or features can be employed in the forming step—step (II)—of this process. Further, it is contemplated that this process for producing an α,β-unsaturated carboxylic acid, or a salt thereof, can employ more than one transition metal-ligand complex, and/or more than one solid promoter (e.g., a mixture of two treated solid oxides), and/or more than one olefin. Additionally, a mixture or combination of two or more diluents can be employed. As above, any suitable reactor, vessel, or container can be used to contact the transition metal-ligand, olefin, diluent, solid promoter (e.g., treated solid oxide), and carbon dioxide, whether using a fixed bed of the solid promoter (e.g., the treated solid oxide), a stirred tank for contacting (or mixing), or some other reactor configuration and process. While not wishing to be bound by the following theory, a proposed and illustrative reaction scheme for this process is provided below (R is H, Na, or K, although not limited thereto):

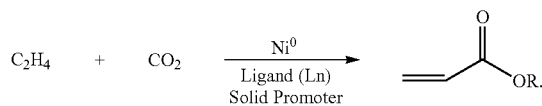

Independently, the contacting and forming steps of any of the processes disclosed herein (i.e., for performing a metallalactone elimination reaction, for producing an α,β-unsaturated carboxylic acid, or a salt thereof), can be conducted at a variety of temperatures, pressures, and time periods. For instance, the temperature at which the components in step (1) or step (I) are initially contacted can be the same as, or different from, the temperature at which the forming step is performed. As an illustrative example, in the contacting step, the components can be contacted initially at temperature T1 and, after this initial combining, the temperature can be increased to a temperature T2 for the forming step (e.g., to form the α,β-unsaturated carboxylic acid, or the salt thereof). Likewise, the pressure can be different in the contacting step and the forming step. Often, the time period in the contacting step can be referred to as the contact time, while the time period in forming step can be referred to as the reaction time. The contact time and the reaction time can be, and often are, different.

In an aspect, the contacting step and/or the forming step of the processes disclosed herein can be conducted at a temperature in a range from 0° C. to 250° C.; alternatively, from 20° C. to 200° C.; alternatively, from 0° C. to 95° C.; alternatively, from 10° C. to 75° C.; alternatively, from 10° C. to 50° C.; or alternatively, from 15° C. to 70° C. In these and other aspects, after the initial contacting, the temperature can be changed, if desired, to another temperature for the forming step. These temperature ranges also are meant to encompass circumstances where the contacting step and/or the forming step can be conducted at a series of different temperatures, instead of at a single fixed temperature, falling within the respective ranges.

In an aspect, the contacting step and/or the forming step of the processes disclosed herein can be conducted at a pressure in a range from 5 to 10,000 psig, such as, for example, from 5 to 2500 psig. In some aspects, the pressure can be in a range from 5 to 500 psig; alternatively, from 25 to 3000 psig; alternatively, from 45 to 1000 psig; or alternatively, from 50 to 250 psig.

The contacting step of the processes is not limited to any particular duration of time. That is, the respective components can be initially contacted rapidly, or over a longer period of time, before commencing the forming step. Hence, the contacting step can be conducted, for example, in a time period ranging from as little as 1-30 seconds to as long as 1-12 hours, or more. In non-continuous or batch operations, the appropriate reaction time for the forming step can depend upon, for example, the reaction temperature, the reaction pressure, and the ratios of the respective components in the contacting step, among other variables. Generally, however, the forming step can occur over a time period that can be in a range from 1 minute to 96 hours, such as, for example, from 2 minutes to 96 hours, from 5 minutes to 72 hours, from 10 minutes to 72 hours, or from 15 minutes to 48 hours.

If the process employed is a continuous process, then the metallalactone/solid promoter catalyst contact/reaction time (or the transition metal-ligand/solid promoter catalyst contact/reaction time) can be expressed in terms of weight hourly space velocity (WHSV)—the ratio of the weight of the metallalactone (or transition metal-ligand complex) which comes in contact with a given weight of solid promoter (e.g., treated solid oxide) per unit time. While not limited thereto, the WHSV employed, based on the amount of the solid promoter (e.g., the treated solid oxide), can be in a range from 0.05 to 100, from 0.05 to 50, from 0.075 to 50, from 0.1 to 25, from 0.5 to 10, from 1 to 25, or from 1 to 5.

In the processes disclosed herein, the molar yield of the α,β-unsaturated carboxylic acid, or the salt thereof), based on the metallalactone (or based on the transition metal of the transition metal-ligand complex) is at least 2%, and more often can be at least 5%, at least 10%, or at least 15%. In particular aspects of this invention, the molar yield can be at least 25%, at least 50%, at least 75%, at least 100%, at least 125%, at least 150%, at least 200%, or at least 350%, and often can range up to 10,000%, or 100,000%, or 1,000,000%, as catalytic efficiencies are realized.

The specific α,β-unsaturated carboxylic acid (or salt thereof) that can be formed or produced using the processes of this invention is not particularly limited. Illustrative and non-limiting examples of the α,β-unsaturated carboxylic acid can include acrylic acid, methacrylic acid, 2-ethylacrylic acid, cinnamic acid and the like, as well as combinations thereof. Illustrative and non-limiting examples of the salt of the α,β-unsaturated carboxylic acid can include sodium acrylate, magnesium acrylate, sodium methacrylate, and the like, as well as combinations thereof.

Once formed, the α,β-unsaturated carboxylic acid (or salt thereof) can be purified and/or isolated and/or separated using suitable techniques which can include, but are not limited to, evaporation, distillation, chromatography, crystallization, extraction, washing, decanting, filtering, drying, and the like, including combinations of more than one of these techniques. In an aspect, the process for performing a metallalactone elimination reaction (or the process for producing an α,β-unsaturated carboxylic acid, or a salt thereof) can further comprise a step of separating or isolating the α,β-unsaturated carboxylic acid (or salt thereof) from other components, such as the diluent and/or the solid promoter (e.g., the treated solid oxide). For instance, a solid-liquid separations technique can be used.

EXAMPLES

The invention is further illustrated by the following examples, which are not to be construed in any way as imposing limitations to the scope of this invention. Various other aspects, modifications, and equivalents thereof which, after reading the description herein, may suggest themselves to one of ordinary skill in the art without departing from the spirit of the present invention or the scope of the appended claims.

The following nickelalactone complexes, which can be derived from $CO_2$-ethylene coupling, were used to evaluate various homogeneous and heterogeneous (solid) promoters in certain examples that follow.

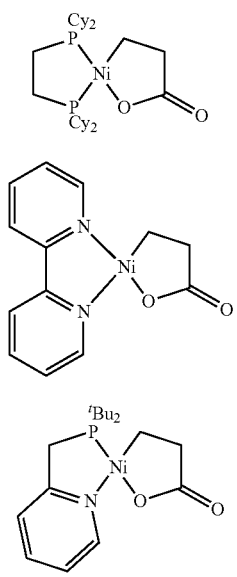

The general nickelalactone elimination reaction was performed as follows. A flask was charged with 10 mg of nickelalactone (A, B, or C), promoter, and approximately 10 mL of diluent. The reaction mixture was heated with vigorous stirring on an oil bath under conditions described in the examples below. The reaction mixture was allowed to cool to ambient temperature, then acidified. The yield of acrylic acid was determined by $^1$H NMR in $D_6$-acetone versus an internal standard sorbic acid stock solution.

Examples 1-8

Evaluation of Homogeneous Activators/Promoters—Acrylate Elimination

For Examples 1-8, 5 equivalents of the activator/promoter (per Ni) were incubated with the nickelalactone (A, B, or C) at 50° C. for 3 hours, followed by eventual acid hydrolysis and extraction to quantify the amount of acrylic acid by $^1$H NMR against an internal standard, as reflected in the following reaction scheme:

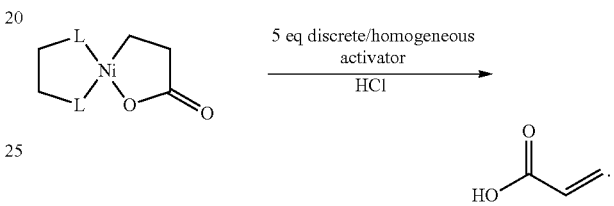

The results of the evaluation of the homogeneous activators/promoters are summarized in Table I. The diluents employed in Example 1 and Examples 2-7 were 5:1 tetrahydrofuran/acetone and tetrahydrofuran, respectively. Example 8 was investigated in tetrahydrofuran, methanol, and acetone. The homogeneous promoter of Example 5 was a solution of methylaluminoxane in toluene, while the homogeneous promoter of Example 6 was a mixture of Mg($^n$Bu)$_2$ and methanol, which results in an alkoxide. As shown in Table I, the homogeneous activators/promoters of Examples 1-8 failed to yield any acrylic acid with any of the nickelalactones investigated.

TABLE I

| Molar Yields of Examples 1-8. | | | | |
|---|---|---|---|---|
| Example | Promoter | A | B | C |
| 1 | Na$_2$(CO$_3$) | 0 | 0 | 0 |
| 2 | Al(CH$_2$CH$_3$)$_3$ | 0 | 0 | 0 |
| 3 | Al(OCH$_2$CH$_3$)$_3$ | 0 | 0 | 0 |
| 4 | Ti(O$^i$Pr)$_4$ | 0 | — | — |
| 5 | (Al(CH$_3$)O)$_n$ | 0 | — | — |
| 6 | Mg($^n$Bu)$_2$ + MeOH | 0 | — | — |
| 7 | Ca(OMe)$_2$ | 0 | — | — |
| 8 | Mg(OH)$_2$ | 0 | — | — |

Notes:
Me = methyl; $^i$Pr = isopropyl; $^n$Bu = n-butyl.

Examples 9-12

Evaluation of Solid/Heterogeneous Activators/Promoters—Acrylate Elimination

Examples 9-12 were performed in a manner similar to that of Examples 2-7, as reflected in the following reaction scheme (25 equivalents per Ni were based on site concentration (mmol/g) of the solid activator/promoter; HCl was used to liberate the acrylic acid for analysis):

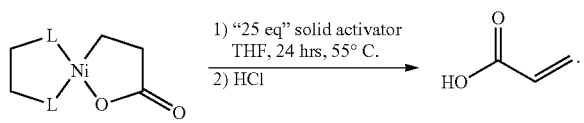

The results of the evaluation of the solid/heterogeneous activators/promoters (calcined at 400° C.) are summarized in Table II. Unexpectedly, in contrast with the homogeneous Al and Mg promoters of Examples 2-3, 5-6, and 8, the solid promoters of Examples 9-12 produced a measurable amount of acrylic acid. More surprisingly, Example 11A and 11C (zirconia) and Example 12A and 12C (magnesia) provided significant molar yields of acrylic acid (from 20% to 90%).

TABLE II

Molar Yields of Examples 9-12.

| Example | Promoter | Site conc. (mmol/g) | A | B | C |
|---|---|---|---|---|---|
| 9 | alumina | 5.4 | 0 | 0 | 11 |
| 10 | silica-magnesia | 5.3 | Trace | 0 | 0 |
| 11 | zirconia | 1.3 | 23 | 0 | 23 |
| 12 | magnesia | 1.1 | 88 | 6 | 58 |

Examples 13-24

Evaluation of Solid/Heterogeneous Activators/Promoters—Acrylate Elimination

Examples 13-24 were performed in a manner similar to that of Examples 9-12, with only nickelalactone A, as reflected in the following reaction scheme (25 equivalents per Ni were based on site concentration (mmol/g) of the solid activator/promoter; HCl was used to liberate the acrylic acid for analysis):

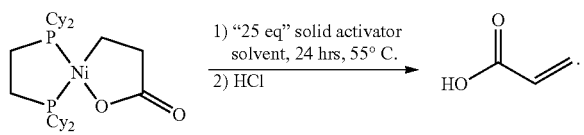

The results of the evaluation of the solid/heterogeneous activators/promoters (calcined at 400° C.) in different diluents/solvents are summarized in Table III. Unexpectedly, alumina, zirconia, magnesia, magnesium aluminate, and sepiolite produced significant amounts of acrylic acid using different diluents, with generally from 5% to 90% molar yield.

Magnesium aluminate was further tested under different calcining conditions. At 400° C. in THF diluent, the yield was 37%. Calcining at 250° C. reduced the yield to 6%, while calcining at 550° C. increased the yield to 47%.

Examples 25-33

Evaluation of Treated Solid Oxides—Acrylate Elimination

Examples 25-33 were performed by mixing 18 μmol of the nickel compound, 18 μmol of the diphosphine ligand, 5 mL of diluent (THF or toluene), and the treated solid oxide (200 mg for Examples 25-30, 50 mg for Examples 31-33) at 60° C. for 30 to 60 minutes, as reflected in the following reaction scheme:

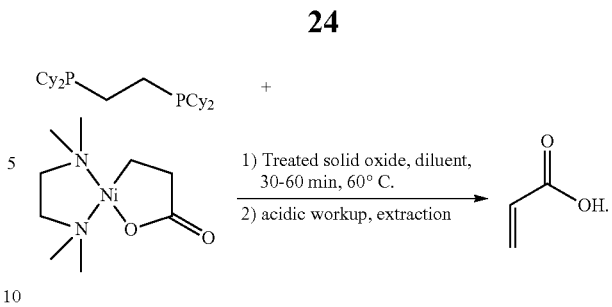

Aqueous sodium bisulfate was used to liberate the acrylic acid for analysis, followed by extraction into $D_2O$/acetone-$d_6$ to quantify the amount of acrylic acid by $^1H$ NMR spectroscopy relative to an internal sorbic acid standard.

The alumina used in Example 30, and used as the base material for Examples 25-29, 34-37, 39, and 41, had a pore volume of 1.3 mL/g and a surface area of 330 m²/g. For Example 30, the alumina was calcined at 500° C. in dry air for 3 hours.

The zinc-treated alumina of Example 25 was prepared by mixing 10 g of alumina with 30 mL of an aqueous solution containing 2.5 g of zinc chloride. After removing the water in a vacuum oven at 90° C. overnight, the dried powder was calcined at 500° C. in dry air for three hours. The calcium-treated aluminas of Examples 27 and 29 were prepared similarly, except that calcining was performed at 600° C. in dry air for 3 hours.

The chlorided alumina of Example 26 was prepared by injecting 3 mL of $CCl_4$ liquid (and vaporizing the $CCl_4$) over a period of less than 1 minute into a nitrogen gas stream used to calcine the alumina at 500° C. for three hours, resulting in chlorided alumina.

The sodium-treated alumina of Example 28 was prepared by mixing 22.8 g of alumina with 60 mL of an aqueous solution containing 4.6 g of sodium bicarbonate. After removing the water in a vacuum oven at 90° C. overnight, the dried powder was calcined at 200° C. in dry air for three hours.

In Example 31 and Example 32, sodium bicarbonate and cesium carbonate, respectively, were calcined at 200° C. in dry air for 6 hours, while in Example 33, sodium carbonate was not calcined (untreated).

The results of the evaluation of the treated solid oxides and untreated sodium carbonate of Examples 25-33 are summarized in Table IV. Unexpectedly, in contrast with the chlorided alumina of Example 26, the treated solid oxides of Examples 25 and 27-30 produced significant amounts of acrylic acid, with molar yields ranging from approximately 3% to 27%. Also unexpectedly, the calcined carbonates of Examples 31-32 yielded acrylic acid, while the uncalcined Example 33 did not.

Examples 34-41

Evaluation of Treated Solid Oxides—Direct Conversion of $CO_2$ and Ethylene to Acrylate Examples 34-41 were performed by mixing 0.1 mmol of the nickel compound, 0.11 mmol of the diphosphine ligand, 500 mL of the diluent, and 1 g of the treated solid oxide in a reactor equilibrated with 150 psig ethylene, followed by 300 psig carbon dioxide, and then heating to 100° C. for 6 hours, as reflected in the following reaction scheme:

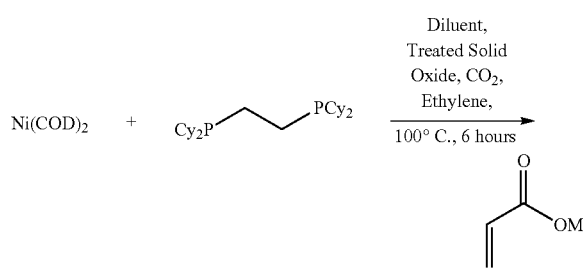

The reaction product was extracted into $D_2O$/acetone-$d_6$ for acrylate yield determination by $^1H$ NMR spectroscopy relative to an internal sorbic acid standard.

The sodium-treated sulfated alumina of Example 34 was prepared by mixing alumina with a solution of sulfuric acid in methanol, to result in approximately 15 wt. % sulfate based on the weight of the sulfated alumina. After drying under vacuum at 110° C. overnight, the dried powder was calcined at 600° C. in dry air for three hours. After cooling, 4.2 g of the sulfated alumina and 2 g of sodium tert-butoxide were combined in 60 mL of toluene, forming a yellow suspension. The mixture was stirred at ambient temperature for 18 hours, filtered, and washed with 10 mL of toluene, forming the colorless solid (sodium-treated sulfated alumina) of Example 34.

The sodium-treated chlorided alumina of Example 36 was prepared using the chlorided alumina of Example 26, and following the same sodium treatment procedure used in Example 34.

The fluorided silica-coated alumina of Example 41 was prepared by first contacting alumina with tetraethylorthosilicate in isopropanol to equal 25 wt. % $SiO_2$. After drying, the silica-coated alumina was calcined at 600° C. for 3 hours. Next, the fluorided silica-coated alumina (7 wt. % F) was prepared by impregnating the calcined silica-coated alumina with an ammonium bifluoride solution in methanol, drying, and then calcining at 600° C. for 3 hours. The sodium-treated fluorided silica-coated alumina of Example 35 was prepared using the fluorided silica-coated alumina of Example 41, and following the same sodium treatment procedure used in Example 34.

The sodium-treated sulfated silica-coated alumina (8 wt. % sulfate) of Example 37 was prepared using silica-coated alumina prepared as described in Example 41, and then sulfating and sodium treating in the manner described in Example 34.

The sodium-treated fluorided silica-alumina of Example 38 used a silica-alumina having 13% alumina by weight, a surface area of 400 m$^2$/g, and a pore volume of 1.2 mL/g, as a base material. This material was mixed with an aqueous solution containing ammonium hydrogen fluoride, dried under vacuum at 110° C. overnight, and calcined at 450° C. in dry air for three hours. The fluorided silica-alumina was then sodium treated in the same manner as described in Example 34.

The sodium-treated tungsten alumina of Example 39 was prepared by first saturating 12.91 g of alumina (surface area of 300 m$^2$, pore volume of 1.2 mL/g, average particle size of 100 microns) with an aqueous solution of 6.341 g of ammonium metatungstate hydrate in 50 mL of deionized water to give a wet sand consistency. After isolating and drying the solid, the solid was calcined at 600° C. for 3 hours. The sodium treatment was performed in the same manner as described in Example 34.

The sodium-treated aluminophosphate of Example 40 was prepared by first adding 100 mL of deionized water to 1 mole of aluminum nitrate nonahydrate, and heating the mixture to 60° C., which resulted in a uniform clear liquid. Then, 0.9 mol of ammonium phosphate dibasic was added and dissolved into the solution. After 1 hour of stirring at 60° C., concentrated ammonium hydroxide was added until gelation occurred, forming a hard solid. The solid was broken up into smaller pieces, and washed three times in 4 L of warm deionized water. A final wash was accomplished in 4 L of n-propanol, followed by filtration, and then drying in a vacuum oven at 110° C. The dried powder was then calcined at 600° C. for 3 hours, and subsequently sodium treated in the manner described in Example 34.

The results of the evaluation of the treated solid oxides of Examples 34-41 are summarized in Table V. Unexpectedly, in contrast with the fluorided silica-coated alumina of Example 41 (which produced no acrylic acid), the treated solid oxides of Examples 34-40 produced significant amounts of acrylic acid, with from 38% to 181% molar yield. The metal-treated chemically-modified solid oxides of Examples 34-35 and 37-38 were particularly successful in catalytically producing acrylic acid directly from $CO_2$ and ethylene, with molar yields in excess of 100% (based on the transition metal of the transition metal-ligand complex).

TABLE III

| | | Molar Yields of Examples 13-24. | | | | | | |
|---|---|---|---|---|---|---|---|---|
| Example | Promoter | Site conc. (mmol/g) | THF | 2,5-Me$_2$THF | Methanol | Acetone | Toluene | Chlorobenzene |
| 13 | Silica | 1.0 | 0 | — | — | 0 | 0 | 0 |
| 14 | Alumina | 5.4 | 10 | — | 0 | 12 | 12 | 38 |
| 15 | silica-alumina | 5.0 | 4 | — | — | 0 | 0 | 0 |
| 16 | aluminum phosphate | 4.0 | 0 | — | — | 0 | 0 | 0 |
| 17 | alumina-boria | 5.4 | trace | — | — | 0 | 0 | trace |
| 18 | silica-magnesia | 5.3 | trace | — | 0 | trace | 0 | 0 |
| 19 | silica-titania | 5.4 | 6 | — | — | 0 | 0 | 0 |
| 20 | Zirconia | 1.3 | 23 | — | 0 | 5 | 0 | — |
| 21 | Magnesia | 1.1 | 88 | 27 | 0 | 33 | 18 | 45 |
| 22 | magnesium aluminate | 1.1 | 37 | 30 | — | — | 43 | 41 |
| 23 | Sepiolite | 2.2 | 17 | — | — | 0 | trace | 12 |
| 24 | Titania | 1.4 | 0 | — | — | 0 | 0 | 0 |

TABLE IV

Examples 25-33.

| Example | Treated Solid Oxide | Calcination Temperature (° C.) | Diluent | Acrylic Acid Molar Yield (%) |
|---|---|---|---|---|
| 25 | ZnCl$_2$-alumina | 500 | THF | 2.8 |
| 26 | CCl$_4$-alumina | 500 | THF | 1.3 |
| 27 | Ca(NO$_3$)$_2$-alumina | 600 | THF | 13.8 |
| 28 | NaHCO$_3$-alumina | 200 | Toluene | 8.5 |
| 29 | Ca(NO$_3$)$_2$-alumina | 600 | Toluene | 27 |
| 30 | alumina | 500 | Toluene | 7.1 |
| 31 | NaHCO$_3$ | 200 | Toluene | 6.2 |
| 32 | CsCO$_3$ | 200 | Toluene | 2.8 |
| 33 | Untreated Na$_2$CO$_3$ | N/A | Toluene | 0 |

TABLE V

Examples 34-41.

| Example | Treated Solid Oxide | Diluent | Acrylate Molar Yield (%) |
|---|---|---|---|
| 34 | NaO$^t$Bu sulfated alumina | Toluene | 102 |
| 35 | NaO$^t$Bu fluorided silica-coated alumina | Toluene | 131 |
| 36 | NaO$^t$Bu chlorided alumina | Toluene | 38 |
| 37 | NaO$^t$Bu sulfated silica-coated alumina | Toluene | 181 |
| 38 | NaO$^t$Bu fluorided silica-alumina | Toluene | 118 |
| 39 | NaO$^t$Bu tungsten alumina | Toluene | 76 |
| 40 | NaO$^t$Bu aluminophosphate | Toluene | 95 |
| 41 | fluorided silica-coated alumina | Toluene | 0 |

The invention is described above with reference to numerous aspects and specific examples. Many variations will suggest themselves to those skilled in the art in light of the above detailed description. All such obvious variations are within the full intended scope of the appended claims. Other aspects of the invention can include, but are not limited to, the following (aspects typically are described as "comprising" but, alternatively, can "consist essentially of" or "consist of" unless specifically stated otherwise):

Aspect 1. A process for performing a metallalactone elimination reaction, the process comprising:
(1) contacting
   (a) a metallalactone;
   (b) a diluent; and
   (c) a treated solid oxide; and
(2) forming an α,β-unsaturated carboxylic acid, or a salt thereof.

Aspect 2. The process defined in aspect 1, wherein at least a portion of the diluent comprises the α,β-unsaturated carboxylic acid, or the salt thereof, formed in step (2).

Aspect 3. A process for producing an α,β-unsaturated carboxylic acid, or a salt thereof, the process comprising:
(1) contacting
   (a) a metallalactone;
   (b) a diluent; and
   (c) a treated solid oxide;
(2) forming an adduct of an α,β-unsaturated carboxylic acid adsorbed onto the treated solid oxide; and
(3) treating the adduct adsorbed onto the treated solid oxide to produce the α,β-unsaturated carboxylic acid, or the salt thereof.

Aspect 4. The process defined in aspect 3, wherein at least a portion of the diluent comprising a transition metal of the metallalactone is removed after step (2).

Aspect 5. The process defined in any one of aspects 1-4, wherein in step (1), the metallalactone and the diluent contact a fixed bed of the treated solid oxide.

Aspect 6. The process defined in any one of aspects 1-4, wherein in step (1), the metallalactone and the treated solid oxide are contacted by mixing/stirring in the diluent.

Aspect 7. The process defined in any one of aspects 3-6, wherein the treating step comprises contacting the adduct adsorbed onto the treated solid oxide with any suitable acid, or any acid disclosed herein, e.g., HCl, sodium bisulfate, or acetic acid.

Aspect 8. The process defined in any one of aspects 3-6, wherein the treating step comprises contacting the adduct adsorbed onto the treated solid oxide with any suitable base, or any base disclosed herein, e.g., carbonates (e.g., Na$_2$CO$_3$, Cs$_2$CO$_3$, MgCO$_3$), hydroxides (e.g., Mg(OH)$_2$, NaOH), or alkoxides (e.g., Al(O$^i$Pr)$_3$, Na(O$^t$Bu), Mg(OEt)$_2$).

Aspect 9. The process defined in any one of aspects 3-6, wherein the treating step comprises contacting the adduct adsorbed onto the treated solid oxide with any suitable solvent, or any solvent disclosed herein, e.g., carbonyl-containing solvents such as ketones, esters, or amides (e.g., acetone, ethyl acetate, N,N-dimethylformamide), alcohol solvents, or water.

Aspect 10. The process defined in any one of aspects 3-6, wherein the treating step comprises heating the adduct adsorbed onto the treated solid oxide to any suitable temperature, or a temperature in any range disclosed herein, e.g., from 50° C. to 1000° C., from 100° C. to 800° C., from 150° C. to 600° C., or from 250° C. to 550° C.

Aspect 11. The process defined in any one of the preceding aspects, further comprising a step of contacting a transition metal-ligand complex with an olefin and carbon dioxide (CO$_2$) to form the metallalactone.

Aspect 12. A process for producing an α,β-unsaturated carboxylic acid, or a salt thereof, the process comprising:
(I) contacting
   (i) a transition metal-ligand complex;
   (ii) an olefin;
   (iii) carbon dioxide (CO$_2$);
   (iv) a diluent; and
   (v) a treated solid oxide; and
(II) forming the α,β-unsaturated carboxylic acid, or the salt thereof.

Aspect 13. The process defined in aspect 11 or 12, wherein the olefin comprises any suitable olefin or any olefin disclosed herein, e.g., ethylene, propylene, or 1-butene.

Aspect 14. The process defined in any one of aspects 1-13, wherein the α,β-unsaturated carboxylic acid, or a salt thereof, comprises any suitable α,β-unsaturated carboxylic acid, or any α,β-unsaturated carboxylic acid disclosed herein, or a salt thereof, e.g., acrylic acid, methacrylic acid, 2-ethylacrylic acid, cinnamic acid, sodium acrylate, magnesium acrylate, or sodium methacrylate.

Aspect 15. The process defined in any one of aspects 1-14, wherein the molar yield of the α,β-unsaturated carboxylic acid, or the salt thereof, based on the metallalactone (or based on the transition metal of the transition metal-ligand complex) is in any range disclosed herein, e.g., at least 5%, at least 10%, at least 15%, at least 25%, at least 50%, at least 100%, at least 150%, or at least 200%.

Aspect 16. The process defined in any one of aspects 1-15, wherein the process further comprises a step of isolating the α,β-unsaturated carboxylic acid, or the salt thereof, e.g., using any suitable separation/purification procedure or any separation/purification procedure disclosed herein, e.g., evaporation, distillation, or chromatography.

Aspect 17. The process defined in any one of aspects 1-16, wherein the contacting step and/or the forming step is/are conducted at any suitable pressure or at any pressure disclosed herein, e.g., from 5 psig to 10,000 psig, or from 45 psig to 1000 psig.

Aspect 18. The process defined in any one of aspects 1-17, wherein the contacting step and/or the forming step is/are conducted at any suitable temperature or at any temperature disclosed herein, e.g., from 0° C. to 250° C., from 0° C. to 95° C., or from 15° C. to 70° C.

Aspect 19. The process defined in any one of aspects 1-18, wherein the contacting step is conducted at any suitable weight hourly space velocity (WHSV) or any WHSV disclosed herein, e.g., from 0.05 to 50, from 1 to 25, or from 1 to 5, based on the amount of the treated solid oxide.

Aspect 20. The process defined in any one of aspects 1-19, wherein the treated solid oxide is a Lewis acid.

Aspect 21. The process defined in any one of aspects 1-19, wherein the treated solid oxide is a Brønsted base.

Aspect 22. The process defined in any one of aspects 1-19, wherein the treated solid oxide is a Brønsted base and a Lewis acid.

Aspect 23. The process defined in any one of aspects 1-22, wherein the treated solid oxide comprises any suitable solid oxide, or any solid oxide disclosed herein.

Aspect 24. The process defined in aspect 23, wherein the solid oxide comprises $Al_2O_3$, $B_2O_3$, $BeO$, $Bi_2O_3$, $CdO$, $Co_3O_4$, $Cr_2O_3$, $CuO$, $Fe_2O_3$, $Ga_2O_3$, $La_2O_3$, $Mn_2O_3$, $MoO_3$, $Na_2O$, $NiO$, $P_2O_5$, $Sb_2O_5$, $SiO_2$, $SnO_2$, $SrO$, $ThO_2$, $TiO_2$, $V_2O_5$, $WO_3$, $Y_2O_3$, $ZnO$, $ZrO_2$, $K_2O$, $CaO$, $La_2O_3$, or $Ce_2O_3$, including mixed oxides thereof, and combinations thereof.

Aspect 25. The process defined in aspect 23, wherein the solid oxide comprises silica, alumina, titania, zirconia, magnesia, boria, calcia, zinc oxide, silica-alumina, silica-coated alumina, silica-titania, silica-zirconia, silica-magnesia, alumina-titania, alumina-zirconia, zinc-aluminate, alumina-boria, silica-boria, aluminum phosphate, aluminophosphate, aluminophosphate-silica, magnesium aluminate, titania-zirconia, or a combination thereof.

Aspect 26. The process defined in aspect 23, wherein the solid oxide comprises magnesium aluminate, calcium aluminate, zinc aluminate, zirconium aluminate, sodium aluminate, magnesium zirconium oxide, sodium zirconium oxide, calcium zirconium oxide, lanthanum chromium oxide, barium titanium oxide, or a combination thereof.

Aspect 27. The process defined in aspect 23, wherein the solid oxide comprises sodium carbonate, sodium bicarbonate, potassium carbonate, cesium carbonate, or a combination thereof.

Aspect 28. The process defined in any one of aspects 1-27, wherein the treated solid oxide is a calcined solid oxide.

Aspect 29. The process defined in any one of aspects 1-28, wherein prior to step (1) or step (I), the treated solid oxide is formed by calcining at any suitable temperature, or at a temperature in any range disclosed herein, e.g. from 150° C. to 1000° C., from 200° C. to 750° C., or from 200° C. to 600° C.

Aspect 30. The process defined in any one of aspects 1-27, wherein the treated solid oxide is a metal-treated solid oxide.

Aspect 31. The process defined in aspect 30, wherein prior to step (1) or step (I), the metal-treated solid oxide is produced by a process comprising contacting any suitable solid oxide and any suitable metal-containing compound and calcining (concurrently and/or subsequently).

Aspect 32. The process defined in aspect 30 or 31, wherein the metal-treated solid oxide comprises an alkali metal, an alkaline earth metal, a transition metal, or any combination thereof, and generally at an amount in a range from 1 to 30 wt. %, from 5 to 25 wt. %, or from 6 to 18 wt. %, based on the total weight of the metal-treated solid oxide.

Aspect 33. The process defined in any one of aspects 30-32, wherein the metal-treated solid oxide comprises an alkali metal (an alkali metal-treated solid oxide), e.g., sodium, potassium, or cesium, as well as combinations thereof.

Aspect 34. The process defined in any one of aspects 30-32, wherein the metal-treated solid oxide comprises an alkaline earth metal (an alkaline earth metal-treated solid oxide), e.g., magnesium, calcium, or barium, as well as combinations thereof.

Aspect 35. The process defined in any one of aspects 30-32, wherein the metal-treated solid oxide comprises a transition metal (a transition metal-treated solid oxide), e.g., titanium, zirconium, hafnium, tungsten, or zinc, as well as combinations thereof.

Aspect 36. The process defined in any one of aspects 1-27, wherein the treated solid oxide is a metal-treated chemically-modified solid oxide.

Aspect 37. The process defined in aspect 36, wherein prior to step (1) or step (I), the metal-treated chemically-modified solid oxide is produced by a process comprising contacting any suitable solid oxide and any suitable electron-withdrawing anion and calcining (concurrently and/or subsequently) to form the chemically-modified solid oxide, and contacting the chemically-modified solid oxide with any suitable metal-containing compound.

Aspect 38. The process defined in aspect 36 or 37, wherein the metal-treated chemically-modified solid oxide comprises an alkali metal, an alkaline earth metal, a transition metal, or any combination thereof, and generally at an amount in a range from 1 to 30 wt. %, from 5 to 25 wt. %, or from 6 to 18 wt. %, based on the total weight of the metal-treated chemically-modified solid oxide.

Aspect 39. The process defined in any one of aspects 36-38, wherein the metal-treated chemically-modified solid oxide comprises an alkali metal (an alkali metal-treated chemically-modified solid oxide), e.g., sodium, potassium, or cesium, as well as combinations thereof.

Aspect 40. The process defined in any one of aspects 36-38, wherein the metal-treated chemically-modified solid oxide comprises an alkaline earth metal (an alkaline earth metal-treated chemically-modified solid oxide), e.g., magnesium, calcium, or barium, as well as combinations thereof.

Aspect 41. The process defined in any one of aspects 36-38, wherein the metal-treated chemically-modified solid oxide comprises a transition metal (a transition metal-treated chemically-modified solid oxide), e.g., titanium, zirconium, hafnium, tungsten, or zinc, as well as combinations thereof.

Aspect 42. The process defined in any one of aspects 36-41, wherein the chemically-modified solid oxide comprises a solid oxide contacted with an electron-withdrawing anion, e.g., any solid oxide and any electron-withdrawing anion disclosed herein.

Aspect 43. The process defined in aspect 42, wherein (a) the solid oxide comprises silica, alumina, silica-alumina, silica-coated alumina, aluminum phosphate, aluminophosphate, heteropolytungstate, titania, zirconia, magnesia, boria, zinc oxide, a mixed oxide thereof, or any mixture thereof, and (b) the electron-withdrawing anion comprises sulfate, bisulfate, fluoride, chloride, bromide, iodide, fluorosulfate, fluoroborate, phosphate, fluorophosphate, trifluoroacetate, triflate, fluorozirconate, fluorotitanate, phosphotungstate, tungstate, or any combination thereof.

Aspect 44. The process defined in any one of aspects 36-43, wherein the solid oxide comprises alumina, silica-alumina, silica-coated alumina, or a mixture thereof.

Aspect 45. The process defined in any one of aspects 36-44, wherein the electron-withdrawing anion comprises sulfate, fluoride, chloride, or any combination thereof.

Aspect 46. The process defined in any one of aspects 36-44, wherein the electron-withdrawing anion comprises sulfate.

Aspect 47. The process defined in any one of aspects 36-44, wherein the electron-withdrawing anion comprises fluoride, chloride, or both.

Aspect 48. The process defined in any one of aspects 36-43, wherein the chemically-modified solid oxide comprises fluorided alumina, chlorided alumina, bromided alumina, sulfated alumina, tungstated alumina, fluorided silica-alumina, chlorided silica-alumina, bromided silica-alumina, sulfated silica-alumina, fluorided silica-zirconia, chlorided silica-zirconia, bromided silica-zirconia, sulfated silica-zirconia, fluorided silica-titania, fluorided silica-coated alumina, fluorided-chlorided silica-coated alumina, sulfated silica-coated alumina, phosphated silica-coated alumina, or any combination thereof.

Aspect 49. The process defined in any one of aspects 36-43, wherein the chemically-modified solid oxide comprises chlorided alumina, fluorided silica-alumina, fluorided silica-coated alumina, fluorided-chlorided silica-coated alumina, sulfated alumina, sulfated silica-coated alumina, or a combination thereof.

Aspect 50. The process defined in any one of aspects 1-29, wherein the treated solid oxide comprises calcined sodium carbonate, calcined sodium bicarbonate, calcined potassium carbonate, calcined cesium carbonate, or a combination thereof.

Aspect 51. The process defined in any one of aspects 1-31, wherein the treated solid oxide comprises sodium-treated alumina, potassium-treated alumina, cesium-treated alumina, sodium-treated aluminophosphate, or a combination thereof.

Aspect 52. The process defined in any one of aspects 1-31, wherein the treated solid oxide comprises magnesium-treated alumina, calcium-treated alumina, barium-treated alumina, or a combination thereof.

Aspect 53. The process defined in any one of aspects 1-31, wherein the treated solid oxide comprises zinc-treated alumina, zirconium-treated alumina, sodium-tungsten-treated alumina, or a combination thereof.

Aspect 54. The process defined in any one of aspects 1-31, wherein the treated solid oxide comprises sodium-treated chlorided alumina, sodium-treated sulfated alumina, sodium-treated tungstated alumina, sodium-treated sulfated silica-coated alumina, sodium-treated fluorided silica-coated alumina, sodium-treated fluorided silica-alumina, sodium-treated fluorided-chlorided silica-coated alumina, or a combination thereof.

Aspect 55. The process defined in any one of aspects 1-54, wherein the treated solid oxide has any suitable surface area, or a surface area in any range disclosed herein, e.g., from 10 $m^2/g$ to 750 $m^2/g$, from 20 $m^2/g$ to 500 $m^2/g$, or from 30 $m^2/g$ to 350 $m^2/g$.

Aspect 56. The process defined in any one of aspects 1-55, wherein the treated solid oxide has any suitable pore volume, or a pore volume in any range disclosed herein, e.g., from 0.1 mL/g to 2.5 mL/g, from 0.1 mL/g to 1.5 mL/g, or from 0.2 mL/g to 1.0 mL/g.

Aspect 57. The process defined in any one of aspects 1-56, wherein the diluent comprises any suitable non-protic solvent, or any non-protic solvent disclosed herein.

Aspect 58. The process defined in any one of aspects 1-56, wherein the diluent comprises any suitable weakly coordinating or non-coordinating solvent, or any weakly coordinating or non-coordinating solvent disclosed herein.

Aspect 59. The process defined in any one of aspects 1-56, wherein the diluent comprises any suitable carbonyl-containing solvent, or any carbonyl-containing solvent disclosed herein, e.g., ketones, esters, or amides (e.g., acetone, ethyl acetate, or N,N-dimethylformamide).

Aspect 60. The process defined in any one of aspects 1-56, wherein the diluent comprises any suitable ether solvent, or any ether solvent disclosed herein, e.g., THF, dimethyl ether, diethyl ether, or dibutyl ether.

Aspect 61. The process defined in any one of aspects 1-56, wherein the diluent comprises any suitable aromatic hydrocarbon solvent, or any aromatic hydrocarbon solvent disclosed herein, e.g., benzene, xylene, or toluene.

Aspect 62. The process defined in any one of aspects 1-56, wherein the diluent comprises any suitable halogenated aromatic hydrocarbon solvent, or any halogenated aromatic hydrocarbon solvent disclosed herein, e.g., chlorobenzene or dichlorobenzene.

Aspect 63. The process defined in any one of aspects 1-56, wherein the diluent comprises THF, 2,5-Me$_2$THF, methanol, acetone, toluene, chlorobenzene, pyridine, or a combination thereof.

Aspect 64. The process defined in any one of aspects 1-63, wherein the transition metal of the metallalactone (or of the transition metal-ligand complex) is a Group 8-11 transition metal.

Aspect 65. The process defined in any one of aspects 1-63, wherein the transition metal of the metallalactone (or of the transition metal-ligand complex) is Fe, Co, Ni, Cu, Ru, Rh, Pd, Ag, Ir, Pt, or Au.

Aspect 66. The process defined in any one of aspects 1-63, wherein the transition metal of the metallalactone (or of the transition metal-ligand complex) is Ni, Fe, or Rh.

Aspect 67. The process defined in any one of aspects 1-63, wherein the metallalactone is a nickelalactone, e.g., any suitable nickelalactone or any nickelalactone disclosed herein.

Aspect 68. The process defined in any one of aspects 1-67, wherein the ligand of the metallalactone (or of the transition metal-ligand complex) is any suitable neutral electron donor group and/or Lewis base, or any neutral electron donor group and/or Lewis base disclosed herein.

Aspect 69. The process defined in any one of aspects 1-67, wherein the ligand of the metallalactone (or of the transition metal-ligand complex) is a bidentate ligand.

Aspect 70. The process defined in any one of aspects 1-69, wherein the ligand of the metallalactone (or of the transition metal-ligand complex) comprises at least one of a nitrogen, phosphorus, sulfur, or oxygen heteroatom.

Aspect 71. The process defined in any one of aspects 1-69, wherein the ligand of the metallalactone (or of the transition metal-ligand complex) is any suitable carbene group or any carbene group disclosed herein.

Aspect 72. The process defined in any one of aspects 1-69, wherein the metallalactone, ligand, or transition metal-ligand complex is any suitable metallalactone, ligand, or transition metal-ligand complex, or is any metallalactone, ligand, or transition metal-ligand complex disclosed herein.

We claim:

1. A process for producing an α,β-unsaturated carboxylic acid, or a salt thereof, the process comprising:
(I) contacting
(i) a transition metal-ligand complex;
(ii) an olefin;
(iii) carbon dioxide ($CO_2$);
(iv) a diluent; and
(v) a treated solid oxide comprising an alkali metal-treated chemically-modified solid oxide, an alkaline earth metal-treated chemically-modified solid oxide, or a combination thereof; and
(II) forming the α,β-unsaturated carboxylic acid, or the salt thereof;
wherein the treated solid oxide does not have an organic basic moiety that is covalently bound with a linking moiety to the treated solid oxide; and
wherein the molar yield of the α,β-unsaturated carboxylic acid, or the salt thereof, based on the transition metal of the transition metal-ligand complex, is at least 50%.

2. The process of claim 1, wherein the treated solid oxide comprises an alkali metal-treated chemically-modified solid oxide.

3. The process of claim 1, wherein:
the α,β-unsaturated carboxylic acid, or the salt thereof, comprises acrylic acid, methacrylic acid, 2-ethylacrylic acid, cinnamic acid, sodium acrylate, magnesium acrylate, sodium methacrylate, or a combination thereof; and
the molar yield of the α,β-unsaturated carboxylic acid, or the salt thereof, based on the transition metal of the transition metal-ligand complex, is from 75% to 10,000%.

4. The process of claim 1, wherein:
the olefin comprises ethylene; and
the α,β-unsaturated carboxylic acid comprises acrylic acid.

5. The process of claim 1, wherein the transition metal of the transition metal-ligand complex is a Group 8-11 transition metal, and the ligand of the transition metal-ligand complex is a neutral electron donor group or Lewis base.

6. The process of claim 1, wherein the alkali metal-treated chemically-modified solid oxide comprises:
sodium, potassium, cesium, or a combination thereof; and
a fluorided solid oxide and/or a sulfated solid oxide.

7. The process of claim 1, wherein the alkaline earth metal-treated chemically-modified solid oxide comprises:
magnesium, calcium, barium, or a combination thereof; and
a fluorided solid oxide and/or a sulfated solid oxide.

8. The process of claim 1, wherein the treated solid oxide comprises sodium-treated chlorided alumina, sodium-treated sulfated alumina, sodium-treated sulfated silica-coated alumina, sodium-treated fluorided silica-coated alumina, sodium-treated fluorided silica-alumina, sodium-treated fluorided-chlorided silica-coated alumina, or a combination thereof.

9. The process of claim 1, wherein:
the olefin comprises ethylene;
the α,β-unsaturated carboxylic acid comprises acrylic acid; and
the molar yield of the α,β-unsaturated carboxylic acid, or the salt thereof, based on the transition metal of the transition metal-ligand complex, is at least 75%.

10. A process for producing an α,β-unsaturated carboxylic acid, or a salt thereof, the process comprising:
(1) contacting
(a) a metallalactone;
(b) a diluent; and
(c) a treated solid oxide comprising a calcined solid oxide, a metal-treated solid oxide, a metal-treated chemically-modified solid oxide, or a combination thereof;
(2) forming an adduct of an α,β-unsaturated carboxylic acid adsorbed onto the treated solid oxide; and
(3) contacting the adduct adsorbed onto the treated solid oxide with an acid to produce the α,β-unsaturated carboxylic acid, or the salt thereof;
wherein the molar yield of the α,β-unsaturated carboxylic acid, or the salt thereof, based on the metallalactone, is at least 5%.

11. The process of claim 10, wherein the metallalactone comprises:

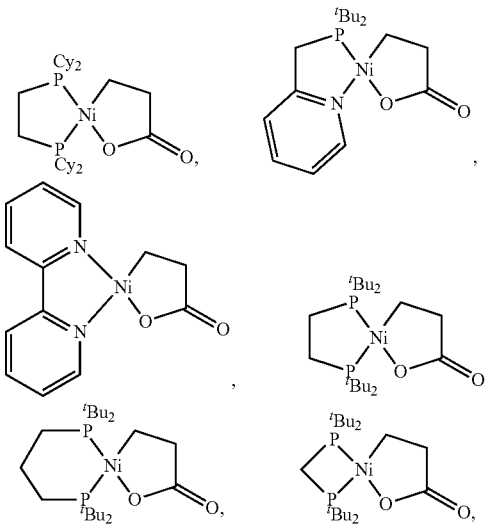

or a combination thereof, wherein Cy is cyclohexyl and $^tBu$ is tert-butyl.

12. The process of claim 10, wherein the molar yield of the α,β-unsaturated carboxylic acid, or the salt thereof, based on the metallalactone, is from 10% to 10,000%.

13. The process of claim 12, wherein:
the metallalactone is a nickelalactone;
the α,β-unsaturated carboxylic acid comprises acrylic acid; and
the treated solid oxide comprises a metal-treated solid oxide, a metal-treated chemically-modified solid oxide, or a combination thereof.

14. The process of claim 10, wherein:
the treated solid oxide comprises a metal-treated solid oxide; and
prior to step (1), the metal-treated solid oxide is produced by a process comprising contacting a solid oxide and a metal-containing compound and calcining.

15. A process for performing a metallalactone elimination reaction, the process comprising:
(1) contacting
(a) a metallalactone;
(b) a diluent; and
(c) a treated solid oxide comprising an alkali metal-treated chemically-modified solid oxide, an alkaline earth metal-treated chemically-modified solid oxide, or a combination thereof; and (2) forming an α,β-unsaturated carboxylic acid, or a salt thereof;
wherein the treated solid oxide does not have an organic basic moiety that is covalently bound with a linking moiety to the treated solid oxide; and
wherein the molar yield of the α,β-unsaturated carboxylic acid, or the salt thereof, based on the metallalactone, is at least 5%.

16. The process of claim 15, wherein in step (1), the metallalactone and the diluent contact a fixed bed of the treated solid oxide.

17. The process of claim 16, wherein
the molar yield of the α,β-unsaturated carboxylic acid, or the salt thereof, based on the metallalactone, is from 50% to 10,000%; and
the metallalactone is a nickelalactone.

18. The process of claim 15, wherein:
prior to step (1), the treated solid oxide is produced by a process comprising contacting a solid oxide and an electron-withdrawing anion and calcining to form the chemically-modified solid oxide, and contacting the chemically-modified solid oxide with an alkali metal and/or alkaline earth metal-containing compound.

19. The process of claim 18, wherein the α,β-unsaturated carboxylic acid comprises acrylic acid.

20. The process of claim 19, wherein the treated solid oxide comprises sodium-treated chlorided alumina, sodium-treated sulfated alumina, sodium-treated sulfated silica-coated alumina, sodium-treated fluorided silica-coated alumina, sodium-treated fluorided silica-alumina, sodium-treated fluorided-chlorided silica-coated alumina, or a combination thereof.

* * * * *